US006083745A

United States Patent [19]
Gudkov et al.

[11] Patent Number: 6,083,745
[45] Date of Patent: *Jul. 4, 2000

[54] GENES AND GENETIC ELEMENTS ASSOCIATED WITH CONTROL OF NEOPLASTIC TRANSFORMATION IN MAMMALIAN CELLS

[75] Inventors: Andrei Gudkov, Glencoe, Ill.; Alexander Kazarov, Baltimore, Md.; Ilya Mazo, Redwood City, Calif.; Igor B. Roninson, Wilmette, Ill.

[73] Assignee: University of Illinois, Urbana, Ill.

[ * ] Notice: This patent is subject to a terminal disclaimer.

[21] Appl. No.: 09/081,167

[22] Filed: May 18, 1998

Related U.S. Application Data

[60] Division of application No. 08/204,740, Mar. 2, 1994, Pat. No. 5,753,432, and a continuation-in-part of application No. 08/033,086, Mar. 9, 1993, abandoned, which is a continuation-in-part of application No. PCT/US91/07492, Oct. 11, 1991, and a continuation-in-part of application No. 07/599,730, Oct. 19, 1990, Pat. No. 5,217,889.

[51] Int. Cl.$^7$ .............................. C12N 5/10; C12N 15/63; C12N 15/11

[52] U.S. Cl. ........................ 435/325; 435/320.1; 536/23.1

[58] Field of Search ............................ 435/6, 325, 320.1; 536/23.1

[56] References Cited

U.S. PATENT DOCUMENTS 5,217,889  6/1993  Roninson et al. .......................... 435/6

OTHER PUBLICATIONS

Ogawa et al. Amino acid sequence of S–adenosyl–L–homocysteine hydrolase from rat liver as derived from the cDNA sequence. Proc. Natl. Acad. Sci. USA vol. 84 pp. 719–723, 1987.
Chen et al. Cell 47:381–389 (1986).
Holzmayer et al. Nucleic Acids Res 20:711–717 (1992).
Gudkov et al. Proc. Natl. Acad. Sci.(1993).
Uhlmann and Peyman Chemical Reviews 90: 543–584 (1990).
Schneider & Banner, Tethrahedron Letters 31:335 (1990).
Culver et al. Science 256:1550–1552 (1992).
Miller & Rosman, Biotechniques 7:980–986 (1989).
Bodine et al Proc Natl Acad Sci USA 87:3738–3742 (1990).
Baim et al. Proc Natl Acad Sci USA 88:5072–5076 (1991).
Endow, Trends Biochem Scie 16: 221–225 (1991).
Navone et al. J Cell Biol 117: 1263–1275 (1992).
Lau and Nathans, EMBO J. 4:3145–3151 (1985).
Noonan et al Proc Natl Acad Sci USA 87:7160–7164 (1990).
Tsai–Pflugfleder et al. Proc. Natl. Acad. Sci USA 85:7177–7181 (1988).
Markowitz et al., Virology 167: 400–406 (1988).
Baltimore et al., Nature 335:395–396 (1988).
Green et al., Cell 58:215–223.
Rimsky et al., Nature 341: 453–456 (1989).
Trono et al., Cell 59:113–120 (1989).
Ransome et al., Proc. Natl. Acad. Sci. USA 87:3806–3810 (1990).
Whitaker–Dowling et al., Virology 175:358–364 (1990).
Lee et al., J. Bacteriol 171:3002–3007 (1989).
Chejanovsky et al., J. Virol. 64: 1764–1770 (1990).
van der Krol et al., Biotechniques 6:958–976 (1988).
Ch'ng et al., Proc. Natl. Acad. Sci. 86: 10006–10010 (1989).
Daugherty et al., Gene Anal. Tech. 6:1–16 (1989).
Powell et al., Proc. Natl. Acad. Sci, USA 86:6949–6952 (1989).
Sarver et al., Science 247:1222–1225 (1990).
Kerr et al., Eur. J. Biochem 175:65–73 (1998).
Bunnell et al., Somat. Cell Mol. Genet. 16: 151–162 (1990).
Keown et al., Methods Enzymol 185: 527–536 (1990).
Murphy and Efstatiadis, Proc. Natl. Sci. USA 84:8277–8281.
Davis et al., Microbiology, Harper and Row, Philadelphia, PA (1980).
Patterson et al., Methods Enzymol 151:121 (1982).
Groger et al., Gene 81: 285–294 (1989).
Rio et al., Science 227:23–28 (1985).
Kosak and Kabat, J. Virol 64 3500–3508 (1990).
Gussow et al., J. Immunol. 139: 3132–3138 (1987).
Patanjali et al., Proc. Natl. Acad. Sci. USA 88:1943–1947 (1991).
Ohara et al., Proc. Natl. Acad. Sci. USA 86:5673–5677 (1989).
Kosik et al., J. Biol. Chem. 265: 3278–3283 (1990).
Murphy & Schmike Nucleic Acids Res. 19: 3403–3408 (1991).
Kim et al., J. Biol. Chem 267: 23113–23121.
Lock et al., J. Cancer 42(3): 371–381 (1988).
Shen et al., Science 232:643–645 (1986).
Sczakiel G. et al. Bioch. Biophys. Res. Comm. 169(2):643–651 (1990).
Napoli C., The Plant Cell 2(4):279–289(1990).
Kidd V.J. et al., Chemical Abstracts 111(23).
Herskowitz, Nature, 329:219–222 (1987).
Friedman et al., Nature 335:452–454 (1988).
Baird et al., J. Bacteriol 172:1587–1594 (1990).
Deiss et al., Science vol. 252:117–120 (1991).
Kinzler et al., 1987, Science 236: 70–73.
Schwab et al., 1989, 1989, Oncogene 4:139–144.
Nakatani et al., Jpn. J. Cancer Res. 81:707–710.
Hunter, 1991, Cell 64: 249–270.
Weinberg 1991, Science 254:1138–1146.
Fearon et al., 1990, Science 247: 49–56.
Sap et al., 1986, Nature 324:635–640.
Weinberger et al., 1986, Nature 324: 641–646.

(List continued on next page.)

*Primary Examiner*—John S. Brusca
*Attorney, Agent, or Firm*—McDonnell Boehnen Hulbert & Berghoff

[57] ABSTRACT

The invention provides genetic suppressor elements that confer the transformed phenotype of malignant mammalian cells upon untransformed cells, methods for identifying and obtaining such elements, methods for isolating and identifying genes corresponding to such elements, and methods of using such elements. The invention also provides genes corresponding to the GSEs of the invention.

3 Claims, 25 Drawing Sheets

OTHER PUBLICATIONS

Xu et al., 1990, Cell 62: 599–608.
Ballester et al., 1990, Cell 63: 851–859.
Buchberg et al., 1990, Nature 347:291–294.
Babacid, 1987, Ann. Rev. Biochem. 56: 779–827.
Fields et al., 1990 Science, 249: 1046–1049.
Raycroft et al., 1990, Science 249: 1049–1051.
Viskochil et al., 1990, Cell 62: 187–192.
Vogelstein et al., 1988, N. Engl. J. Med. 319:525–532.
Solomon et al., 1991, Science, 254: 1153–1160.
Laforgia et al., 1991, Proc. Natl. Acad. Sci. USA 88: 5036–5040.
Trent et al., 1989, Cancer Res. 49:420–423.
Milner et al., 1991, Molec. Cell. Biol. 11: 12–19.
Eliyahu et al., 1984, Nature 312: 646–659.
Parada et al., 1984, Nature 312: 649–651.
Graf & Beug, 1983, Cell 34: 7–9.
Damm et al., 1989, Nature 339: 593–597.
Montenarh & Quasier, 1989, Oncogene 4: 379–382.
Finlay et al., 1988, Molec. Cell Biol. 8: 531–539.
Damm et al., 1987, EMBO J. 6: 375–382.
Sap et al., 1989, Nature, 340:242–244.
Pauwels et al., 1988, J. Virol. Meth. 20: 309–321.
Wolos et al., 1993, J. Immunol, 150:3264–3273.
Kern et al., 1991, Oncogene 6: 131–136.
O'Rourke et al., 1990, Oncogene 5: 1829–1832.
Kern et al., 1991, Science 252: 1708–1711.
Lee et al., 1987, Nature 329: 642–645.
Friend et al., 1987, Proc. Natl. Acad. Sci. USA 84:9059–9063.
Call et al., 1990, Cell 60: 509–520.
Gessler et al., 1990, Nature 343: 774–778.
Duerre et al., 1992, Biochem. Biolog. Cell. 70:703–711.
Perlaky et al., 1992, Cancer Res. 52: 428–436.

```
GTTATGTAAC CCTGGCTATT CTGGAACTTG ATATCTAGAC CAGGCTGGCC TTGAACTCA:
ACAGATATCT TCCTGTTTCT GTCTCCTTAG TGCTGGGATA CAGTGTTTAG TGCTGCCATG
CTGGGTGGGA AGAGTATAAT AATAGCTCAT AGTTACTATG TTTGTTTAGG TTAGACATT:
TTTTTCTGC TTTGTGTGTC TAATATGTTT GAACATCTCA TCTCTTTGAA ACTTGATGTG
GCTGTGTGAT TTGCTTTGGT TATTGAAAAG TGGCACATTG GCCAT
```

Figure 5

LNCX                    LNC(Tr6)
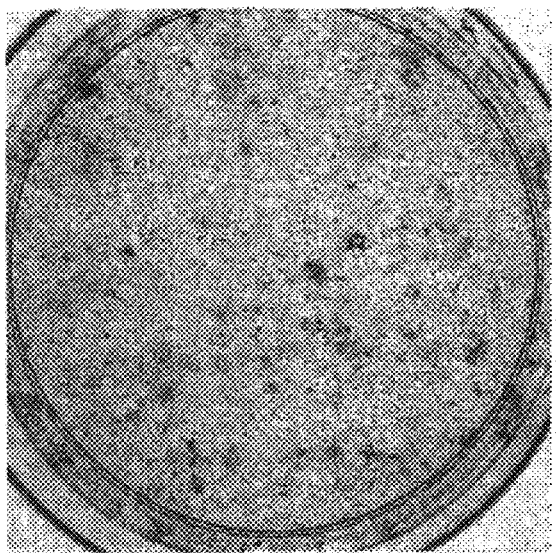 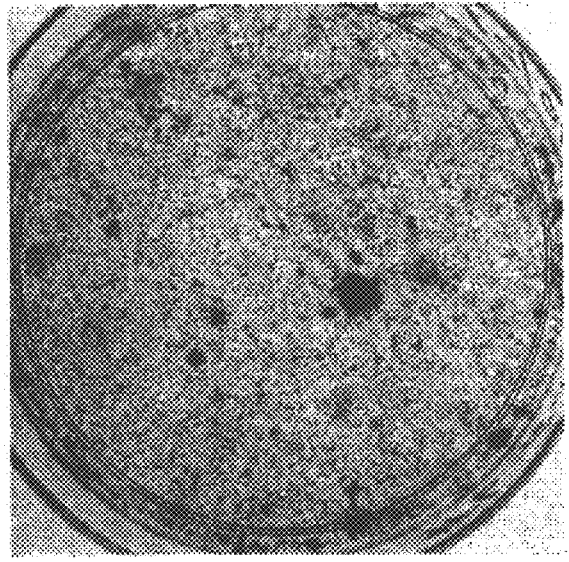
Focus assay
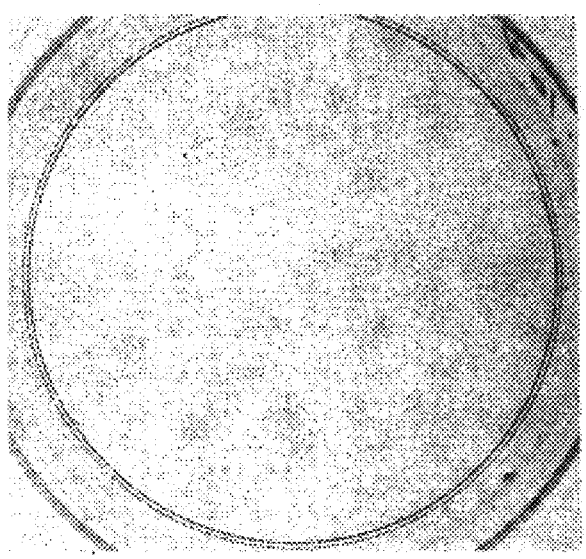 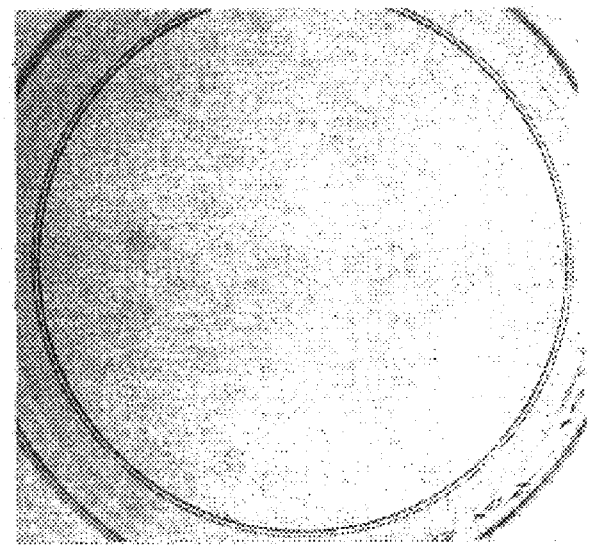
Immortalization assay
Figure 6A

Figure 9

```
CATTCACTGA GTTCATCAGT CCTAGCGGAA GCCGCCAGCA TGTCTGATAA ACTGCCCTAC
AAAGTCGCGG ACATGGACT GGCCGCCTGG GGACGGAAGG CTCTGGATAT AGCTGAGAAT
GAGATGCCAG GGTTGATGCG CATGCGGGAG ATGTACTCAG CCTCCAAGCC ACTGAAGGGT
GCTCGCATTG CTGGCTGCCT GCGCATGACC GTGGAGACTG CTGTTCTCAT TGAGACTCTC
GTGGCCCTGG GTGCTGAGGC GCGGTGGTCC AGCTGCAACA TCTTC
```

Figure 10

```
  0                                                CATTCACTGAGTTCATCAGTCCTAGCGGAAGCCGCCAGCATGTCTGATA
                                                   *   *    *     *****         *    ****************
  0 GGCCCAGCCCCCTTGCGCCTTCCATCA------CGAGTGCCGCCAGCATGTCTGACA
                                                               ** *****************

49 AACTGCCCTACAAAGTCGCGGACACATCGGACTGGCCGCCTGGGGACGGAAGGCTCTGGATA
    ***************          ** ***** ****  ***************
 53 AACTGCCCTACAAAGTCGCCGACACATCGGACTGGCCTGCCTGGGGACGCCAAGGCCCTGACA

109 TAGCTGAGAATGAGATGCCAGGGTTGATGCGCATGCGGGAGATGTACTCAGCCTCCAAGC
    * *******  **** *** ** *  * ****** ******** * ******** ****
113 TTGCTGAGAACGAGATGCCGGGCCTGATGCGGTATGCGGGAGCGGTACTCGGCCTCCAAGC

169 CACTGAAGGGTGCTCTCGCATTGCTGCTGCCTGCGCATGACCGTGGAGACTGCTGTTCTCA
    ********  **   ** * ***** ** *  *  ******** ******* ** ****
173 CACTGAAGGGCCGCCCCGCATCGCTGCTGCCTGCACATGACCGTGGAGACGGCCGTCCTCA

229 TTGAGACTCTCGTGGCCCTGGGCTGAGGCGGTGCTCCAGCTGCAACATCTTC
    ****** **   * ****             ** ******************
233 TTGAGACCCTCGTCACCCTGGGTGCTGAGGTGCAGTGTGTCCAGCTGCAACATCTTC
```

Figure 11

```
  0  EAQPPSPVSITSAASMSDKLPYKVADIGLAAWGRKALDIAENEMPGLMRMRERYSASKPL
        *      .  .::.   ************************ **********  ******
  0  ......HSLSSS--VLAEAASMSDKLPYKVADIGLAAWGRKALDIAENEMPGLMRMREMYSASKPL

60  KGARIAGCLHMTVETAVLIETLVTLGAEVQWSSCNIF
     *********.*************  ***..*.****
 58  KGARIAGCLRMTVETAVLIETLVALGAEARWSSCNIF
```

Figure 12

```
AACACGCCGT ACTTCCTCTG CTCAGCCCGT CTTTCCTCAT CATTGACCTT TTGTGTAGGC
AAGAGAACCC TCTGGGTGCA GTTTCATCTG CGGCTAAAGG ATCTCGCTGG CTCCGGTGGA
CCAGGTGAAA AGACACAGCT TTCTTCTTCT CTATAAAGGG CTTTTTCTTT CTGTGAGGCA
TAATGAGGCA GGGACACCCT CTCCGGAACC
```

Figure 16

```
GGATGATGGA GGTGGCAGCT GCCGATGTCC AGAGGCTGGG GGGCTCCGTG GAACTGGTGG
ATATCGGGAA GCAGAAGCTC CCAGATGGCT CGGAGATACC ACTTCTCCCA TCTGCTGGGC
AAGCTAGGCA GCGACCCCCA GAAGAAAACC GTGTGCATTT ACGGCACCT GGACGTGCAG
CCTGCGCCCT GGAGGACGGG TGGGACAGCG AGCCCTTCAC CTTGGTGGAG CGGGAAGGCA
AGCTGTATGG GAGAGGCTCC ACGGACGATA AGG
```

Figure 17

```
CCCGGCCAAT CACCCTTCGG ACCAACACCT TGAAACCCG  TCGCCGAGAC CTTGCTTCAGG
CTCTGATCAA TCGTGGGTT  AATCTGGATC CACTGGGAA  GTGGTCAAAG TCTGGACTTG
TGGTATATGA TTCTTCAGTG CCTATTGGTG CTACCCCTGA GTACCCTCGCT GGACACTATA
TGCTGCAGGG AGCTTCCAGT ATGTTGCCCG TCATGGCCCT GGCACCCTCAG GAGCATGAGC
GGATCTTAGA CATGTGCTGT GCT
```

Figure 18

```
   0 CCCGGCCAATCACCCTTCGGACCAACACCCTTGAAAACCCGTGCCGAGACCTTGCTCAGG
     *****  * ***** **** ***** * *********** ****** ************
 919 CTCGGGCCCGTCACCCTCCGGACCAATACCCTTGAAAACCCGAGACGCCGAGACCTTGCACAGG

60 CTCTGATCAATCGTGGGGTTAATCTGGATCCACTGGGAAGTGGTCAAAGTCTGGACTTG
     *** ** ***** ******* *** *** * **** ***** *** ** ****** **
 979 CTCTAATCAATCGTGGGGTTAACCTGGATCCCCTGGGCAAGTGGTCAAAGACTGGACTAG

120 TGGTATATGATTCTTCAGTGCCTATTGGTGCTACCCCTGAGTACCTCGCTGACACTATA
     *** * ************ ****** ******** ***** ****** ***** ****
1039 TGGTGTATGATTCTTCTGTGCCCATTGGTGCTACCCCCGAGTACCTGGCTGGCACTACA

180 TGCTGCAGGGAGCTTCCAGTATGTTGCCCGTCATGCCCCTGGCACCCTCAGGAGCATGAGC
     ****************** *** *** ***** ***** ****** *** ***********
1099 TGCTGCAGGGAGCCTCCAGTGTGCCCGTCATGCCCCTGGCCTTGGCACCCCAGGAACATGAGC

240 GGATCTTAGACATGTGCTGTGC
     *****  * ***** ** ****
1159 GGATCCTGGACATGTGTTGTGC
```

Figure 19

```
  1                                                RPITLRTNTLKTRRRDLAQALINRGVNLDPLGKWSKSGL
                                                   **·*****************************.****
300 KLMDLFPLSELVEFLEANEVPRPVTLRTNTLKTRRRDLAQALINRGVNLDPLGKWSKTGL

39 VVYDSSVPIGATPEYLAGHYMLQGASSMLPVMALAPQEHERILDMCCA
    ************************************************
360 VVYDSSVPIGATPEYLAGHYMLQGASSMLPVMALAPQEHERILDMCCA
```

Figure 20
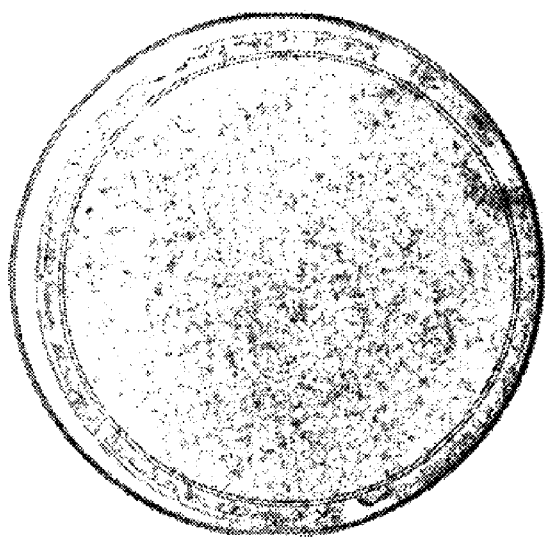
LNCX
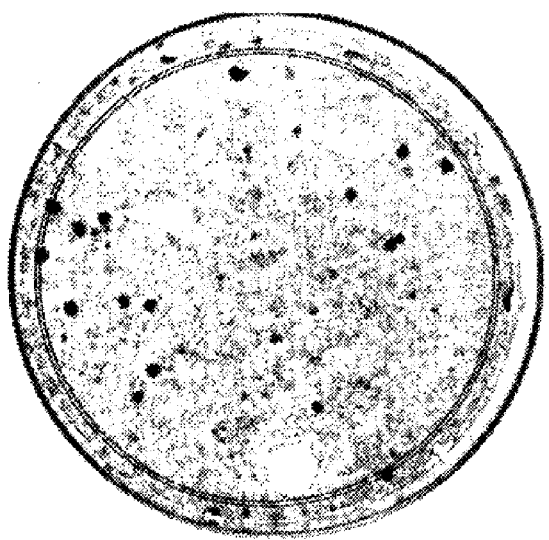
LNC(1bb1)

GENES AND GENETIC ELEMENTS ASSOCIATED WITH CONTROL OF NEOPLASTIC TRANSFORMATION IN MAMMALIAN CELLS

This is a divisional of U.S. patent application Ser. No. 08/204,740, filed Mar. 2, 1994, now U.S. Pat. No. 5,753,432, issued May 19, 1998, and is a continuation-in-part of U.S. Ser. No. 08/033,086, filed Mar. 9, 1993, now abandoned, which in turn is a continuation-in-part of International Patent Application Serial No. PCT/US91/07492, filed on Oct. 11, 1991 and which entered the National stage in the U.S. on Apr. 15, 1993, and is a continuation-in-part of U.S. Ser. No. 07/599,730, filed Oct. 19, 1990, now U.S. Pat. No. 5,217,889, issued Jun. 8, 1993.

This invention was made with government support under grants CA39365 and CA-56738 by the National Institutes of Health. The government has certain rights in the invention.

BACKGROUND OF THE INVENTION

1. Field of the Invention

The invention relates to genes and genetic suppressor elements associated with the control of neoplastic transformation of mammalian cells. More particularly, the invention relates to methods for identifying such genes and genetic suppressor elements as well as to uses for such genes and genetic suppressor elements. The invention specifically provides genetic suppressor elements derived from genes associated with the transformed phenotype of mammalian cells, and therapeutic and diagnostic uses related thereto. The invention also provides genes associated with the control of neoplastic transformation of mammalian cells.

2. Summary of the Related Art

Cancer remains one of the leading causes of death in the United States. Clinically, a broad variety of medical approaches, including surgery, radiation therapy and chemotherapeutic drug therapy are currently being used in the treatment of human cancer (see the textbook *CANCER: Principles & Practice of Oncology*, 2d Edition, De Vita et al., eds., J. B. Lippincott Company, Philadelphia, Pa., 1985). However, it is recognized that such approaches continue to be limited by a fundamental lack of a clear understanding of the precise cellular bases of malignant transformation and neoplastic growth.

The beginnings of such an understanding of the cellular basis of malignant transformation and neoplastic growth have been elucidated over the last ten years. Growth of normal cells is now understood to be regulated by a balance of growth-promoting and growth-inhibiting genes, known as proto-oncogenes and tumor suppressor genes, respectively. Proto-oncogenes are turned into oncogenes by regulatory or structural mutations that increase their ability to stimulate uncontrolled cell growth. These mutations are therefore manifested as dominant (e.g. mutant RAS genes) or co-dominant (as in the case of amplification of oncogenes such as N-MYC or HER2/NEU) (see Varmus, 1989, "A historical overview of oncogenes", in *Oncogenes and the Molecular Origin of Cancer*, Weinberg, ed., Cold Spring Harbor Press, Cold Spring Harbor, N.Y., pp. 3–44).

Dominant and co-dominant genes can be effectively identified and studied using many different techniques based on gene transfer or on selective isolation of amplified or overexpressed DNA sequences (Kinzler et al., 1987, *Science* 236: 70–73; Schwab et al., 1989, *Oncogene* 4: 139–144; Nakatani et al., *Jpn. J. Cancer Res.* 81: 707–710). Expression selection has been successfully used to clone a number of cellular oncogenes. The dominant nature of the oncogenes has facilitated the analysis of their function both in vitro, in cell culture, and in vivo, in transgenic animals. Close to fifty cellular oncogenes have been identified so far (Hunter, 1991, *Cell* 64: 249–270).

It is likely, however, that there are at least as many cancer-associated genes that are involved in suppression rather than induction of abnormal cell growth. This class of genes, known as anti-oncogenes or tumor suppressors, has been defined as comprising "genetic elements whose loss or inactivation allows a cell to display one or another phenotype of neoplastic growth deregulation" by Weinberg (1991, *Science* 254: 1138–1146). Changes in a tumor suppressor gene that result in the loss of its function or expression are recessive, because they have no phenotypic consequences in the presence of the normal allele of the same gene. The recessive nature of mutations associated with tumor suppressors makes such genes very difficult to analyze or identify by gene transfer techniques and explains why oncogene research is far more advanced than studies of tumor suppressors.

In normal cells, tumor suppressor genes may participate in growth inhibition at different levels, from the recognition of a growth inhibiting signal and its transmission to the nucleus, to the induction (or inhibition) of secondary response genes that finally determine the cellular response to the signal, The known tumor suppressor genes have indeed been associated with different steps of the regulatory pathway. Thus, the DCC and ErbA genes encode receptors of two different classes (Fearon et al., 1990, *Science* 247: 49–56; Sap et al., 1986, *Nature* 324: 635–640; Weinberger et al., 1986, *Nature* 324: 641–646). The gene NF-1 encodes a polypeptide that resembles ras-interacting proteins, that are members of the signaling pathway (Xu et al., 1990, *Cell* 62: 599–608; Ballester et al., 1990, *Cell* 62: 851–859; Buchberg et al., 1990, *Nature* 347: 291–294; Barbacid, 1987, *Ann. Rev. Biochem.* 56: 779–827). p53, RB and WT genes encode nuclear regulatory proteins (Fields et al., 1990, *Science* 249: 1046–1049; Raycroft et al., 1990, *Science* 249: 1049–1051; Kern et al., 1991, *Oncogene* 6: 131–136; O'Rourke et al., 1990, *Oncogene* 5: 1829–1832; Kern et al., 1991, *Science* 252: 1708–1711; Lee et al., 1987, *Nature* 329: 642–645; Friend et al., 1987, *Proc. Natl. Acad. Sci. USA* 84: 9059–9063; Call et al., 1990, *Cell* 60: 509–520; Gessler et al., 1990, *Nature* 343: 774–778).

Two approaches have been previously used for cloning tumor suppressor genes. The first approach is based on isolating the regions associated with nonrandom genetic deletions or rearrangements observed in certain types of tumors. This approach requires the use of extremely laborious linkage analyses and does not give any direct information concerning the function of the putative suppressor gene (Friend et al., 1991, *Science* 251: 1366–1370; Viskochil et al., 1990, *Cell* 62: 187–192; Vogelstein et al., 1988, *N. Engl. J. Med.* 319: 525–532). In fact, among numerous observations of loss of heterozygosity in certain tumors (Solomon et al., 1991, *Science* 254: 1153–1160; LaForgia et al., 1991, *Proc. Natl. Acad. Sci. USA* 88: 5036–5040; Trent et al., 1989, *Cancer Res.* 49: 420–423), there are only a few examples where the function of the affected gene is understood. In two of these rare cases the gene function was identified using another method, analysis of dominant negative mutant proteins (Herskowitz, 1987, *Nature* 329: 219–222).

Specifically, the tumor suppressor genes erbA and p53 were first discovered as altered forms which encoded mutant proteins (Sap et al., 1986, ibid.; Weinberger et al., 1986, ibid.; Raycroft et al., 1990, ibid.; Milner et al., 1991, *Molec. Cell. Biol.* 11: 12–19). These altered genes were initially classified as oncogenes, since they induced cell transformation when transfected alone or in combination with other oncogenes (ras in the case of p53 and erbB in the case of erbA; see Eliyahu et al., 1984, *Nature* 312: 646–649; Parada et al., 1984, *Nature* 312: 649–651; Graf & Beug, 1983, *Cell* 34: 7–9; Damm et al., 1989, *Nature* 339: 593–597). Later, however, it was recognized that both of these "oncogenes" acted by interfering with the normal function of the corresponding wild-type genes. Thus, the oncogenic mutant p53 protein forms functionally inactive complexes with the wild-type protein; such complexes fail to provide the normal negative regulatory function of the p53 protein (Herskowitz, 1986, ibid.; Milner et al., 1991, ibid.; Montenarh & Quaiser, 1989, *Oncogene* 4: 379–382; Finlay et al., 1988, *Molec. Cell. Biol.* 8: 531–539). The oncogene erbA, found in chicken erythroblastosis virus, is a mutant version of the chicken gene for thyroid hormone receptor, the transcriptional regulatory protein which participates in tie induction of erythroid differentiation (Damm et al., 1989, ibid.; Damm et al., 1987, *EMBO J.* 6: 375–382). The mutant erbA protein blocks the function of the wild-type receptor by occupying its specific binding sites in the DNA (Sap et al., 1989, *Nature* 340: 242–244).

Thus, naturally arising dominant negative mutants not only allowed the identification of the corresponding tumor suppressor genes but also served as tools for their functional analysis. Such natural tools for recessive gene identification seem to be rare, however, limiting the utility of this approach for the discovery of new tumor suppressor genes.

The discovery and analysis of new recessive genes involved in neoplastic transformation may be greatly accelerated through the use of genetic suppressor elements (GSEs), derived from such genes and capable of selectively suppressing their function. GSEs are dominant negative factors that confer the recessive-type phenotype for the gene to which the particular GSE corresponds. Recently, some developments have been made in the difficult area of isolating recessive genes using GSE technology. Roninson et al., U.S. Pat. No. 5,217,889 (issued Jun. 8, 1993) teach a generalized method for obtaining GSEs (see also Holzmayer et al., 1992, Nucleic Acids Res. 20: 711–717). Gudkov et al., 1993, Proc. Natl. Acad. Sci. USA 90: 3231–3235 teach isolation of GSEs from topoisomerase II cDNA that induce resistance to topoisomerase II-interactive drugs. Co-pending U.S. patent applications Ser. No.08/033,086, filed Mar. 9, 1993, and Ser. No. 08/177,571, filed Jan. 5, 1994, disclosed the discovery by the present inventors of the novel and unexpected result that GSEs isolated from RNA of cells resistant to the anticancer DNA damaging agent, etoposide, include a GSE encoding an antisense RNA homologous to a portion of a kinesin heavy chain gene. Additionally, co-pending U.S. patent application Ser. No. 08/033,086 disclosed two other GSEs from previously-unknown genes, the expression of said GSEs conferring etoposide resistance on mammalian cells. Co-pending U.S. patent application Ser. No. 08/199,900, filed Feb. 22, 1994, disclosed GSEs from previously-unknown genes, the expression of said GSEs conferring cisplatin resistance on mammalian cells.

These results farther underscored the power of the GSE technology developed by these inventors to elucidate recessive gene-mediated biological phenomenon involving unexpected mechanisms, including drug resistance in cancer cells, thereby providing the opportunity and the means for overcoming drug resistance in cancer patients. This technology has now been applied to isolating and identifying GSEs that confer the transformed phenotype of malignant mammalian cells in previously untransformed cells expressing such GSEs, and for isolating and identifying genes associated with, the transformed phenotype.

BRIEF SUMMARY OF THE INVENTION

The invention provides genetic suppressor elements (GSEs) that are random fragments derived from genes associated with the transformed phenotype of malignant mammalian cells, and that confer the transformed phenotype upon cells expressing such GSEs. The invention is based in part on the discoveries disclosed in co-pending U.S. patent applications, Ser. No. 08/033,086, filed Mar. 9, 1993, Ser. No. 08/177,157, filed Jan. 5, 1994, and Ser. No. 08/199,900 filed Feb. 22, 1994, incorporated by reference, providing a method for identifying and isolating GSEs that confer resistance to chemotherapeutic drugs upon cells expressing such GSEs.

In a first aspect, the invention provides a method for identifying GSEs that confer the transformed phenotype on cells expressing the GSEs. This method utilizes selection of cells that harbor clones from a random fragment expression library derived from total cDNA derived from normal cells, preferably normal mouse or human fibroblasts, and subsequent rescue of library inserts from immortalized, morphologically-transformed or frankly tumorigenic cells. In a second aspect, the invention provides a method for identifying and cloning genes that are associated with the transformed phenotype of malignant mammalian cells, and also provides the genes themselves. This method comprises the steps of screening a full length cDNA library with a GSE that confers the transformed phenotype upon cells (or, alternatively, with an oligonucleotide or polynucleotide constituting a portion of such a GSE) and determining the nucleotide sequence of the cDNA insert of any positive clones obtained. Alternatively, the technique of "anchored PCR" (see Example 3 below) can be used to isolate cDNAs corresponding to transformed phenotype-conferring GSEs. Also embodied in this aspect of the invention is isolation of genomic DNA encoding genes associated with the transformed phenotype, for example from genomic DNA libraries. In a third aspect, the invention provides a diagnostic assay for characterizing transformed cells, particularly human tumor cells, that express the transformed phenotype due to the absence of expression or underexpression of a particular gene. This diagnostic assay comprises measuring, preferably quantitatively, the level of expression of the particular gene product by a particular tumor cell sample to be tested, compared with the level of expression in normal, untransformed cells. One feature of this aspect of the invention is the development of antibodies specific for proteins whose underexpression or absence of expression is associated with the transformed phenotype in malignant mammalian, most preferably malignant human, cells. Such antibodies have utility as diagnostic agents for detecting tumor cells in biopsy or other tissue samples, and in characterizing the nature and degree of expression of the transformed phenotype in such cells. In a fourth, the invention provides a starting point for in vitro drug screening and rational design of pharmaceutical products that are useful against tumor cells, i.e., are anticancer agents. By examining the structure, function, localization and pattern of expression of genes associated with the transformed phenotype, strategies can be developed for creating pharmaceutical products that will selectively kill or inhibit the growth of such cells, in which such genes are either not expressed or underexpressed. Also provided by the invention are cultures of mammalian cells which express the transformed phenotype-conferring GSEs of the invention and are transformed thereby. Such cells are useful for determining the physiological and biochemical basis for malignant mammalian cell transformation. Such cells also have utility in the development of pharmaceutical and chemotherapeutic agents for selectively killing or inhibiting the growth of such cells, and thus are ultimately useful in establishing improved chemotherapeutic protocols to more effectively treat neoplastic disease.

Specific preferred embodiments of the present invention will become evident from the following more detailed description of certain preferred embodiments and the claims.

BRIEF DESCRIPTION OF THE DRAWINGS

FIG. 3A illustrates selection of such GSEs via one round of selection for cells that survive crisis; FIG. 3B shows a scheme for re-selection and enrichment of immortalizing GSEs from populations of immortalized MEFs produced according to the scheme shown in FIG. 3A.

FIG. 5 shows the nucleotide sequence of the Tr6-GSE (SEQ ID No.:3).

FIGS. 6A and 6B shows the results of an experiment demonstrating that Tr6GSE (SEQ ID No.:3) is capable of conferring the morphologically transformed phenotype on both Swiss 3T3 cells and MEF cells (FIG. 6A), and is also capable of immortalizing MEF cells in which spontaneous immortalization is suppressed by expression of an exogenously-introduced p53 gene (FIG. 6B).

FIG. 8A shows the results of selection for G418 resistance (as a measure of infection efficiency) and morphological transformation in media supplemented with 5% FCS; FIG. 8B shows the results of PCR analysis of retroviral inserts from genomic DNA of morphologically transformed foci.

FIG. 9 shows the nucleotide sequence of the SAHH-GSE (SEQ ID No.:4).

FIG. 10 shows a comparison between the nucleotide sequence of SAHH-GSE (SEQ ID No.:4) and the SAHH gene sequence (SEQ ID No.:5).

FIG. 11 shows a comparison between the amino acid sequence of the peptide encoded by the SAHH-GSE (SEQ ID No.:6) and the SAHH protein amino acid sequence (SEQ ID No.:7).

FIG. 12 shows the nucleotide sequence of the Tr19-GSE (SEQ ID No.:8).

FIG. 13A, that SAHH-GSE was capable of conferring both immortalization and morphological transformation on MEF cells; FIG. 13B that Tr19-GSE is capable of immortalizing MEF cells; and FIG. 13C that both the SAHH-GSE and an anti-khcs GSE could immortalize MEF cells, but only the SAHH-GSE could morphologically transform MEF cells.

FIG. 16 shows the nucleotide sequence of the Tr22-GSE (SEQ ID No.:9).

FIG. 17 shows the nucleotide sequence of the 1bb1-GSE (SEQ ID No.:10).

FIG. 18 shows a comparison between the nucleotide sequence of the 1bb1-GSE (SEQ ID No.:10) and the P120 human nucleolar antigen gene sequence (SEQ ID No.:11).

FIG. 19 shows a comparison between the amino acid sequence of the peptide encoded by the 1bb1-GSE (SEQ ID No.:12) and a portion of the P120 human nucleolar antigen protein amino acid sequence (SEQ ID No.:13).

FIG. 20 shows the results of a focus-formation assay using infection of Swiss 3T3 cells with retrovirus carrying the 1bb1-GSE (SEQ ID No.:10).

DETAILED DESCRIPTION OF THE PREFERRED EMBODIMENTS

Figure 1:
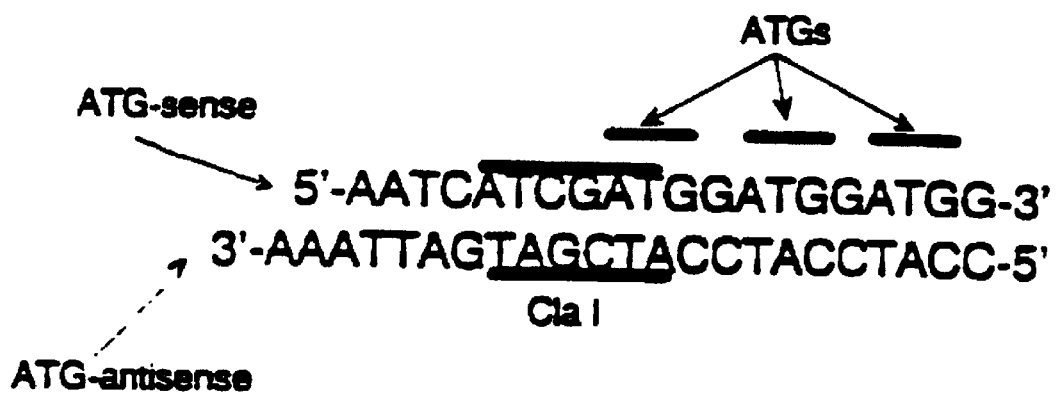
FIG. 1 shows the structure of the adaptor used in cDNA cloning. The nucleotide sequences are shown for the ATG-sense [SEQ.ID.No.:1] and ATG-antisense [SEQ.ID.No.:2] strands of the adaptor.

The invention relates to means for identifying specific gene functions that are associated with the transformed phenotype of malignant mammalian cells. The invention provides genetic suppressor elements (GSEs), the expression of such GSEs conferring the transformed phenotype on untransformed fibroblast cells. The invention further provides methods for identifying such GSEs, as well as methods for their use. For purposes of this invention, the terms "the transformed phenotype of malignant mammalian cells" and "the transformed phenotype" are intended to encompass, but not be limited to, any of the following phenotypic traits associated with cellular transformation of mammalian cells: immortalization, morphological or growth transformation, and tumorigenicity, as detected by prolonged growth in cell culture, growth in semi-solid media, or tumorigenic growth in immuno-incompetent or syngeneic animals.

In a first aspect, the invention provides a method for identifying GSEs that confer upon untransformed cells the transformed phenotype of malignant mammalian cells. The GSEs identified by this method will be homologous to a gene that is associated with the transformed phenotype of malignant mammalian cells. For purposes of the invention, the term "homologous to a gene" has two different meanings, depending on whether the GSE acts through an antisense or antigene mechanism, or through a mechanism of interference at the protein level. In the former case, a GSE that is an antisense or antigene oligonucleotide or polynucleotide is homologous to a gene if it has a nucleotide sequence that hybridizes under physiological conditions to the gene or its mRNA transcript by Hoogsteen or Watson-Crick base-pairing. In the latter case, a GSE that interferes with a protein molecule is homologous to the gene encoding that protein molecule if it has an amino acid sequence that is the same as that encoded by a portion of the gene encoding the protein, or that would be the same, but for conservative amino acid substitutions. In either case, as a practical matter, whether the GSE is homologous to a gene is determined by assessing whether the GSE is capable of inhibiting or reducing the function of the gene.

The method according to this aspect of the invention comprises the step of screening a total cDNA or genomic DNA random fragment expression library phenotypically to identify clones that confer the transformed phenotype on untransformed recipient cells. Preferably, the library of random fragments of total cDNA or genomic DNA is cloned into a retroviral expression vector. In this preferred embodiment, retrovirus particles containing the library are used to infect cells and the infected cells are tested for their ability to exhibit the transformed phenotype, for example, by exhibiting the ability to grow past "crisis" in vitro culture, or to grow in a manner that is recognized as being morphologically-transformed, or to grow in semisolid media, such as soft agar or agarose, or in methylcellulose, or by frankly tumorigenic growth in vivo in an animal. Preferably, the inserts in the library will range from about 100 bp to about 700 bp and more preferably, from about 200 bp to about 500 bp in size. Most preferably, the random fragment library will be a normalized library containing roughly equal numbers of clones corresponding to each gene expressed in the cell type from which it was made, without regard for the level of expression of any gene. However, normalization of the library is unnecessary for the isolation of GSEs that are homologous to abundantly or moderately expressed genes. Once a clonal population of cells that exhibit the transformed phenotype has been isolated, the library clone encoding the GSE is rescued from the cells. At this stage, the insert of the expression library may be tested for its nucleotide sequence. Alternatively, and preferably, the rescued library clone may be further tested for its ability to confer the transformed phenotype in additional transfection or infection and selection assays, prior to nucleotide sequence determination. Determination of the nucleotide sequence, of course, results in the identification of the GSE. This method is further illustrated in Examples 1 and 2.

In a second aspect, the invention provides a method for identifying and cloning genes that are associated with control of neoplastic growth in mammalian cells, as well as the genes derived by this method. This is because GSEs, or portions thereof, can be used as probes to screen full length cDNA or genomic libraries to identify their gene of origin. Alternatively, the technique of "anchored PCR" (see Example 3 below) can be used to isolate cDNAs corresponding to transformed phenotype-conferring GSEs. It will be recognized that the genes associated with control of neoplastic transformation in mammalian cells are sufficiently evolutionarily conserved that the GSEs provided by the invention, or the genes corresponding to such GSEs, can be used as probes to isolate genes corresponding to such neoplastic growth-associated GSEs from any mammalian species, including man.

In some cases, genes that are associated with the transformed phenotype will turn out to be quite surprising. For example, GSEs that have been found to be capable of conferring the transformed phenotype upon untransformed cells include GSEs derived from the mouse homolog of the human P120 nucleolar antigen gene, and the gene for S-adenosyl homocysteine hydrolase, as well as from three GSEs from previously unidentified genes. In addition, a GSE derived from a mouse kinesin gene and associated with etoposide resistance has been previously discovered to be capable of conferring cell culture growth immortalization on mouse embryo fibroblasts (MEF) and normal human fibroblasts, as disclosed in co-pending U.S. patent applications, Ser. No. 08/177,571, filed Jan. 5, 1994, and Ser. No. 08/033,086, filed Mar. 9, 1993. The method according to this aspect of the invention therefore also provides valuable information about the genetic basis for senescence. The method according to this aspect of the invention and its use for studying genes identified thereby and their cellular effects, are further illustrated in Example 3.

In a third aspect, the invention provides a diagnostic assay for characterizing transformed cells, particularly human tumor cells, that express the transformed phenotype due to the absence of expression or underexpression of a particular gene. By using the methods according to the first and second aspects of the invention such a gene is identified and cloned. To determine whether absence of expression or underexpression of such a gene is a naturally occurring, and thus medically significant basis for neoplastic growth and cancer, human tumor cells are assessed for their level of expression of the particular gene of interest. Absence of expression or significantly reduced expression, relative to expression in normal tissues that give rise to the tumor, would then be correlated with the natural history of the particular cancer, including cell and tissue type, incidence, invasiveness, capacity to metastasize, and other relevant properties of the particular tumor. Accordingly, such reduced or absent expression can be the basis for a diagnostic assay for the presence and extent of tumorigenic cells in a tissue sample. Malignant transformation and neoplastic growth as the result of over-expression of a gene is also detectable using similar diagnostic assays provided by the invention. A first embodiment of a diagnostic assay according to this aspect of the invention utilizes an oligonucleotide or oligonucleotides that is/are homologous to the sequence of the gene for which expression is to be measured. In this embodiment, RNA is extracted from a tissue or tumor sample, and RNA specific for the gene of interest is quantitated by standard filter hybridization procedures, an RNase protection assay, or by quantitative cDNA-PCR (see Noonan et al., 1990, *Proc. Natl. Acad. Sci. USA* 87: 7160–7164). In a second embodiment of a diagnostic assay according to this aspect of the invention, antibodies are raised against a synthetic peptide having an amino acid sequence that is identical to a portion of the protein that is encoded by the gene of interest. These antibodies are then used in a conventional quantitative immunoassay (e.g., RIA or immunohistochemical assays) to determine the amount of the gene product of interest present in a sample of proteins extracted from the tumor cells to be tested, or on the surface or at locations within the tumor cells to be tested. In a third embodiment, an enzymatic activity that is a property of a gene associated with neoplastic transformation of cancer cells can be used to measure whether the gene encoding said protein is over- or underexpressed in the cancer cells.

In a fourth aspect, the invention provides a starting point for in vitro drug screening and rational design of pharmaceutical products that can counteract tumorigenicity and neoplastic growth by tumor cells in vivo. In this regard, the invention provides cultures of mammalian cells which express the transformed phenotype-conferring GSEs of the invention and are immortalized and/or transformed thereby. Included within this aspect of the invention are cell cultures that are representative of almost any tissue or cell type. Such cells are useful for determining the physiological and biochemical basis for malignant transformation of mammalian cells, as well as for screening pharmaceutical and chemotherapeutic agents for killing or selectively inhibiting the growth of such transformed cells. Identification of such agents would lead to the development of improved chemotherapeutic protocols to more effectively treat neoplastic disease.

The protein sequence encoded by genes from which the GSEs were derived can be deduced from the cDNA sequence, and the function of the corresponding proteins may be determined by searching for homology with known genes or by searching for known functional motives in the protein sequence. If these assays do not indicate the protein function, it can be deduced through the phenotypic effects of the GSEs suppressing the gene. Such effects can be investigated at the cellular level, by analyzing various growth-related, morphological, biochemical or antigenic changes associated with GSE expression. The GSE effects at the organism level can also be studied by introducing the corresponding GSEs as transgenes in transgenic animals (e.g. mice) and analyzing developmental abnormalities associated with GSE expression. The gene function can also be studied by expressing the full-length cDNA of the corresponding gene, rather than a GSE, from a strong promoter in cells or transgenic animals, and studying the changes associated with overexpression of the gene.

Full-length or partial cDNA sequences can also be used to direct protein synthesis in a convenient prokaryotic or eukaryotic expression system, and the produced proteins can be used as immunogens to obtain polyclonal or monoclonal antibodies. These antibodies can be used to investigate the protein localization and as specific inhibitors of the protein function, as well as for diagnostic purposes. In particular, antibodies raised against a synthetic peptide encoded by the sequence of the GSEs Tr6, Tr19 and Tr22, or the corresponding region of the P120 nucleolar antigen gene or the SAHH gene should be particularly useful (see Examples 2 and 3 and FIGS. 5, 9–11, & 15–18).

Understanding the biochemical function of a gene involved in malignant transformation of mammalian cells is also likely to suggest pharmaceutical means to stimulate or mimic the function of such a gene and thus augment the cytotoxic response to anticancer drugs. For example, if the gene encodes an enzyme producing a certain compound, such a compound can be synthesized chemically and administered in combination with cytotoxic drugs. If a pharmaceutical approach is not apparent from the protein function, one may be able to upmodulate gene expression at the level of transcription. This can be done by cloning the promoter region of the corresponding gene and analyzing the promoter sequence for the presence of cis elements known to provide the response to specific biological stimulators. Such an approach is useful to replace the function of tumor-suppressor genes, for example, to restore the tumor-suppressing function of such genes that has been lost through mutation or other biological insult, resulting in neoplastic disease.

The most straightforward way to increase the expression of gene identified through the GSE approach, the loss of which results in malignant transformation of a cell no longer functionally expressing the gene, would be to insert a full-length cDNA for such a gene into a gene therapy expression vector, for example, a retroviral vector. Such a vector, in the form of a recombinant retrovirus, will be delivered to tumor cells in vivo, and, upon integration, would act to reduce or eliminate neoplastic growth of such cells. The selective delivery to tumor cells can be accomplished on the basis of the selectivity of retrovirus-mediated transduction for dividing cells. Alternatively, the selectivity can be achieved by driving the expression of the gene from a tissue- or tumor-specific promoter, such as, for example, the promoter of the carcinoembryonic antigen gene.

The protein structure deduced from the cDNA sequence can also be used for computer-assisted drug design, to develop new drugs that affect this protein in the same manner as the known anticancer drugs. The purified protein, produced in a convenient expression system, can also be used as the critical component of in vitro biochemical screen systems for new compounds with anticancer activity. In addition, mammalian cells that express tranformed phenotype-conferring GSEs according to the invention are useful for screening compounds for the ability to selectively kill or inhibit the neoplastic growth associated with down-regulation of the corresponding gene.

The following Examples are intended to further illustrate certain preferred embodiments of the invention and are not limiting in nature.

EXAMPLE 1

Generation of a Normalized Random Fragment cDNA Library in a Retroviral Vector and Introduction into Virus-Packaging Cell Lines A normalized cDNA population was prepared as described in co-pending U.S. patent application Ser. No. 08/033,086, filed Mar. 9, 1993, which is incorporated by reference. Briefly, poly(A)$^+$ RNA was purified from total RNA extracted in equal amounts from exponentially-growing and quiescent, confluent monolayer cultures of mouse NIH 3T3 cells, an immortalized mouse cell line known to be useful in cellular transformation assays (see Shih et al., 1979, *Proc. Natl. Acad. Sci. USA* 76: 5714–5718). To avoid over-representation of the 5'-end sequences in a randomly primed cDNA population, RNA was fragmented by boiling for 5 minutes to an average size of 600–1000 nucleotides. These RNA fragments were then used for preparing randomly primed double-stranded cDNA. This randomly primed cDNA was then ligated to a synthetic adaptor providing ATG codons in all three possible reading frames and in a proper context for translation initiation (see FIG. 1). The structure of the adaptor determined its ligation to the blunt-ended fragments of the cDNA in such a way that each fragment started from initiation codons independently from its orientation. The ligated mixture was amplified by PCR, using the "sense" strand of the adaptor as a PCR primer, in twelve separate reactions that were subsequently combined, in order to minimize random over-or under-amplification of specific sequences and to increase the yield of the product. The PCR-amplified mixture was then size-fractionated by electrophoresis in a 6% polyacrylamide gel, and fragments ranging in size from approximately 200–500 basepairs (bps) were selected for further manipulations.

For normalization, the cDNA preparation was denatured and reannealed, using the following time-points for reannealing: 0, 24, 48, 72, 96 and 120 hours. The single-stranded and double-stranded DNAs from each reannealed mixture were then separated by hydroxyapatite chromatography. These DNA fractions from each time point of reannealing were PCR-amplified using adaptor-derived primers and analyzed by slot blot hybridization with probes corresponding to genes expressed at different levels in human cells. α-tubulin and c-myc probes were used to represent highly-expressed genes, adenosine deaminase and topoisomerase-II (using separate probes for the 5' and 3' ends of the latter cDNA) probes were used to represent intermediately-expressed genes, and a c-fos probe was used to represent low-level expressed genes. The fraction that contained similar proportions of high-, medium- and low-expressed genes was used for the library preparation.

The normalized cDNA preparation was cloned into a ClaI site of the MoMLV-based retroviral vector pLNCX, which carries the neo (G418 resistance) gene, expressed under the transcriptional control of the promoter contained in the retroviral long terminal repeat (LTR), and which expresses the cDNA insert sequences from a cytomegalovirus (CMV)-derived promoter (see FIG. 2 and Miller and Rosman, 1989, Biotechniques 7: 980–986). pLNCX contains translation termination codons in all three reading frames within 20 bp downstream of the cloning site comprising SEQ ID NOS.14 and 15. To generate a representative-size library for GSE selection, this ligation mixture was divided into five portions and used to transform E. coli in 5 separate electroporation experiments, using conventional techniques and standard conditions for electroporation (see Sambrook et al., 1992, Molecular Cloning: A Laboratory Manual, Cold Spring Harbor Laboratory Press, Cold Spring Harbor, N.Y.). The transformed bacteria were plated on a total of 500 agar plates (150 mm in diameter) and the plasmid produced (18 mg total) was isolated from the colonies washed off the agar. A total of approximately $5 \times 10^7$ clones were obtained, more than 60% of which carried inserts of normalized cDNA, as estimated by PCR amplification of 50 randomly-picked colonies.

Plasmid DNA was used for in vivo selection of GSEs capable of conferring a transformed phenotype of appropriate cells as discussed in Example 2 below. The plasmid library prepared as described above was converted into a mixture of retroviral particles by transfection into twenty P150 culture plates containing a 1:1 mixture of ecotropic and amphotropic packaging cells (derived from NIH 3T3 cells; see Markowitz et al., 1988, Virology 167: 400–406), the cells having been seeded the day before transfection at a density of $1.5 \times 10^6$ cells per plate. 15 µg of random fragment retroviral library (RFRL) plasmid DNA were transfected per P150 plate. The retrovirus-containing cell culture supernatant was collected every 12 hours over three days post-transfection and purified by filtration through 0.22 µm membranes.

EXAMPLE 2

Introduction of a Retroviral Random Fragment Library into Mouse Fibroblast Cells The purified retrovirus-containing supernatant prepared according to Example 1 was used in each of three assays chosen to detect three distinct aspects of the transformed phenotype in mammalian cells. Selection of transforming GSEs required the use of suitable indicator cells capable of undergoing identifiable and selectable transformation-associated changes. Three different selection protocols for GSEs that induce phenotypic traits associated with neoplastic transformation were used. First, for selection of GSEs capable of immortalizing senescent cells, mouse embryonic fibroblasts were used as the indicator cell system. The other two selection protocols utilized three different types of immortalized mouse fibroblasts, each of which differ in transformation-associated traits, in order to select GSEs specific for different stages of neoplastic transformation. Two of these cell lines are subvariants of NIH 3T3 cells, and the third type of cells comprise several populations of Swiss 3T3 cells, newly established from spontaneously-transformed MEF cells. These latter cells were expected to contain multiple phenotypic variants which would be differentially susceptible to the effects of different GSEs, thereby increasing the number of different types of GSEs that could be detected. Some characteristic properties of each of the three types of immortalized cells are shown in Table I.

TABLE I

| Cell Type | Rate of Spontaneous Focus Formation | Plating Efficiency | Tumorigenicity[a] 3 Weeks | 6 weeks |
|---|---|---|---|---|
| NIH 3T3-HF | $2-5 \times 10^{-6}$ | 20–30% | 0/6 | 5/6 |
| NIH 3T3-LF | $<1 \times 10^{-7}$ | 20–30% | 0/6 | 0/6 |
| Swiss 3T3 | $<1 \times 10^{-7}$ | <0.1% | N.T. | N.T. |

[a] = Number of mice with tumors/Number of mice tested
N.T. = not tested

A. Selection of GSEs Capable of Immortalizing Mouse Embryo Fibroblasts

Figure 3A:
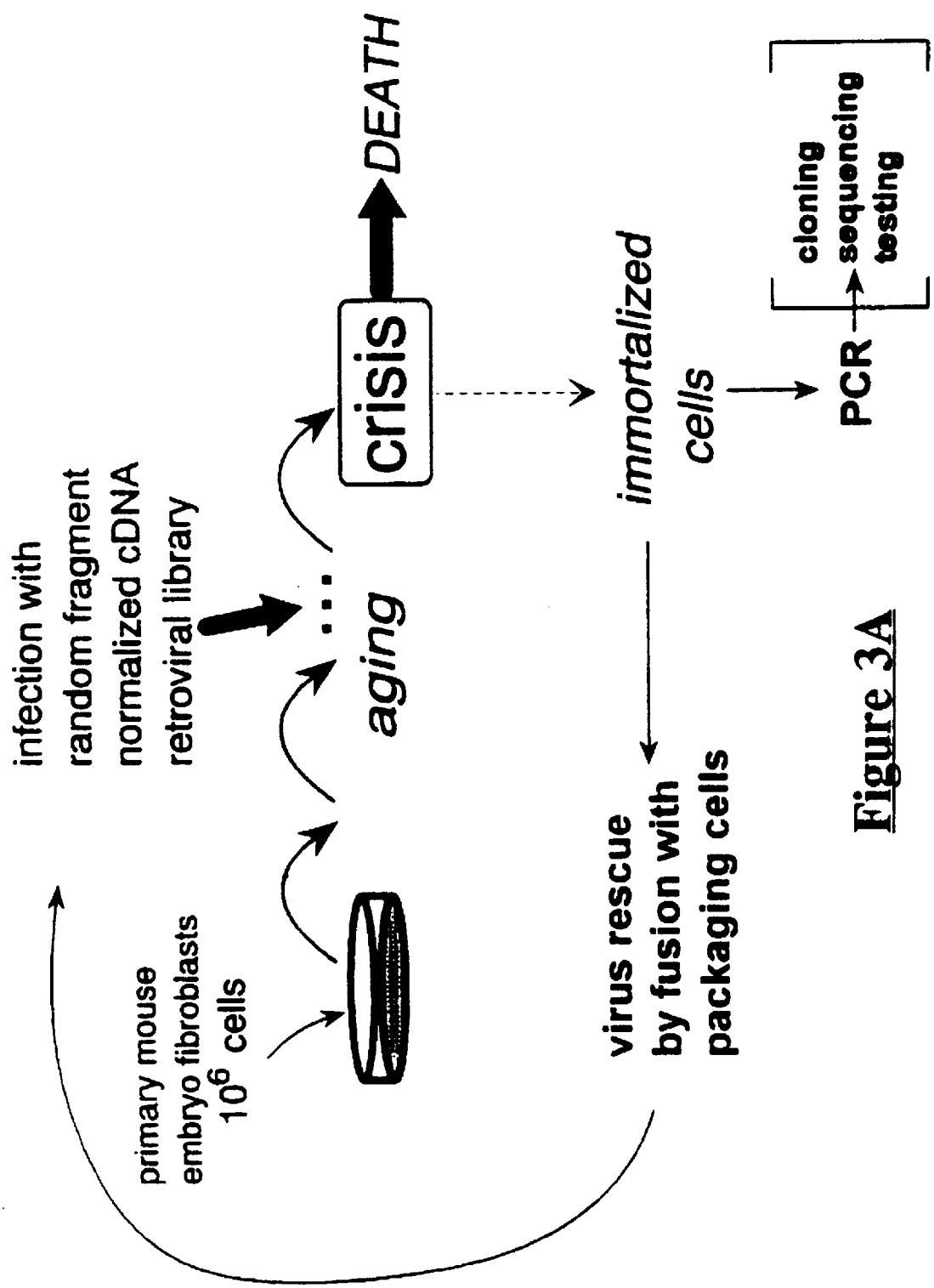
FIGS. 3A and 3B shows a scheme for selection of immortalizing GSEs in MEF cells from a random fragment expression library (RFEL) from mouse NIH 3T3 cell cDNA.

GSE selection for the ability to immortalize senescent cells was carried out on cultures of mouse embryo fibroblast (MEF) cells infected with retroviral particles comprising the RFRL of Example 1, using a protocol depicted in FIG. 3. Primary MEF cultures were prepared from 11-day old Swiss Webster mouse embryos using a conventional trypsinization procedure. Cells were split every three-four days, with $2.5 \times 10^6$ cells plated per P150 culture plate at each passage, grown in Dulbecco's Modified Eagle's medium (DMEM) supplemented with 10% (v/v) fetal calf serum. Additionally, about $5 \times 10^6$ cells were preserved after every second passage until the culture underwent senescence and "crisis", by freezing in a cryogenic protective solution at −70° C. For retroviral infection experiments, cells frozen 4 passages before crisis were thawed and grown in culture on 10 P150 plates at a density of $1 \times 10^6$ cells/plate. The thawed cells were infected with RFRL-derived retrovirus over 3 days, at 12 hour intervals, and MEFs were repeatedly infected with each collected supernatant. Each P150 plate was processed independently beginning with infection with the RFRL-derived retrovirus. The efficiency of infection was estimated by plating equal numbers of infected cells in the presence and absence of G418 for 5 days, at which time relative cell viability was measured using the MTT assay (see Pauwels et al., 1988, J. Virol. Meth. 20: 309–321. Typical infections efficiencies obtained in such assays indicated that about 70% of the MEFs were infected with RFRL-derived retroviruses.

Figure 2:
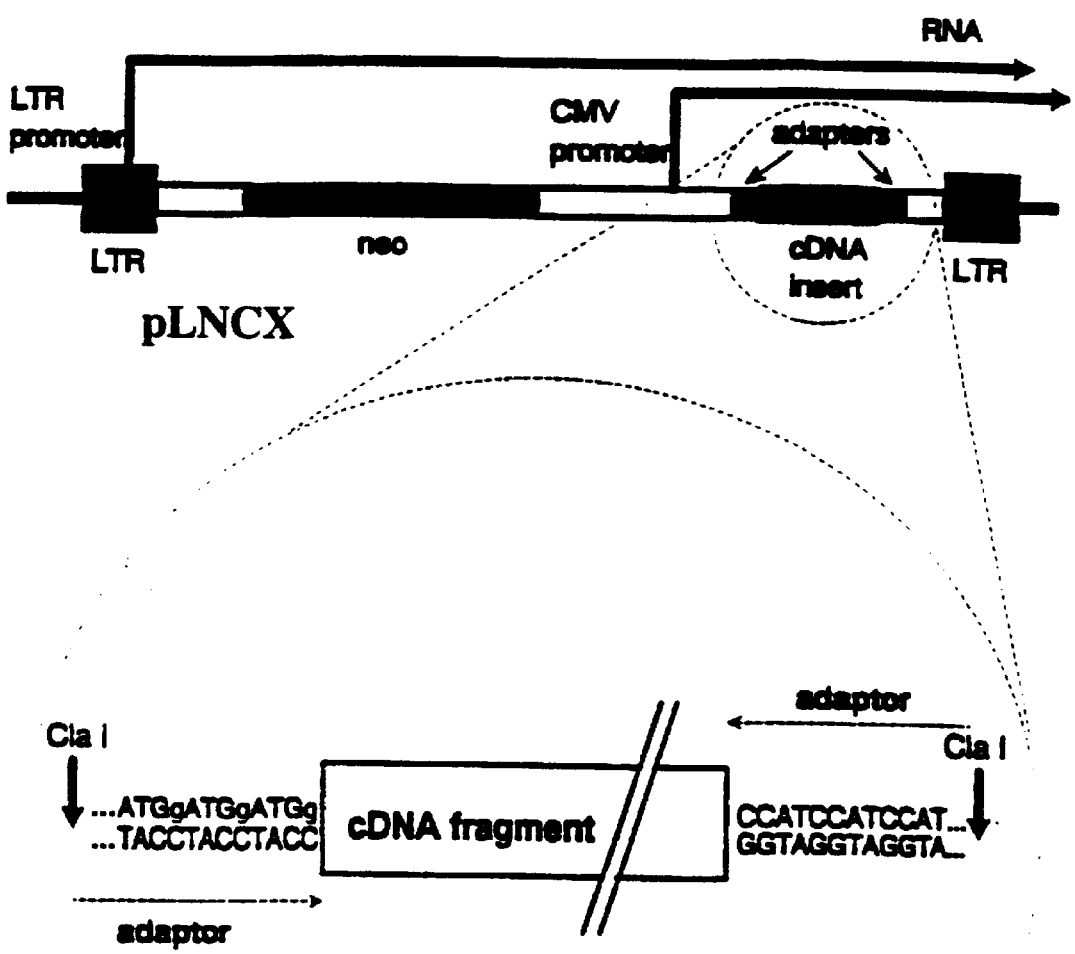
FIG. 2 shows the structure of the pLNCX vector used in cDNA cloning comprising SEQ ID NOS.14 and 15.
Figure 4:
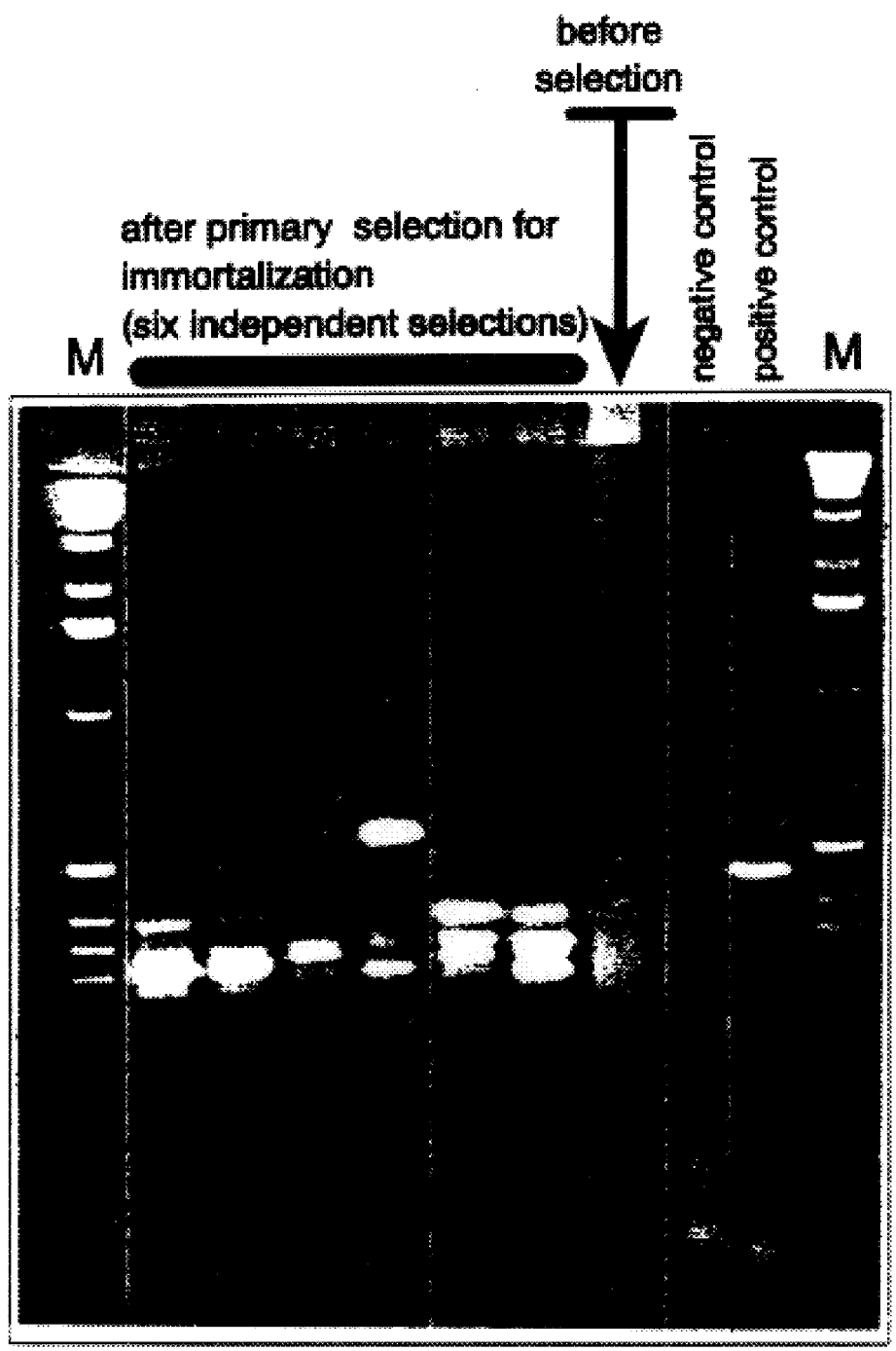
FIG. 4 shows polyacrylamide gel electrophoretic analysis of PCR fragments comprising MEF immortalizing GSE.

After the cell cultures overcame senescence and crisis, the surviving cells from each plate were fused with ecotropic packaging cells to rescue the virus, using polyethylene glycol as previously described in co-pending U.S. patent application Ser. No. 08/199,900, filed on Feb. 22, 1994. The complexity of the rescued virus population was estimated by PCR amplification of proviral inserts, using the oligonucleotide corresponding to the sense strand of the cloning adaptor as PCR primer (as shown in FIG. 4). The PCR products from RFRL-derived retrovirus infected MEF cells initially formed a continuous smear of fragments 200–500 bps in length. As the cells proceeded through crisis, the complexity of the cDNA inserts decreased, and separate bands became visible (FIG. 2).

The rescued viral preparations from post-crisis cells, containing the virus at relatively low titre ($\sim 10^4$/mL), were used to infect fresh populations of pre-crisis MEF cells, which were then allowed to go through crisis. The efficiency of these secondarily-infected cells was estimated by G418 selection before and after crisis; in several secondary selection experiments, the proportion of infected cells increased after crisis, suggesting enrichment for GSE-carrying cells. PCR analysis performed on cellular DNA from immortalized cells surviving this second round selection indicated the selection of several cDNA inserts, containing putative immortalization-conferring GSEs.

Figure 3B:
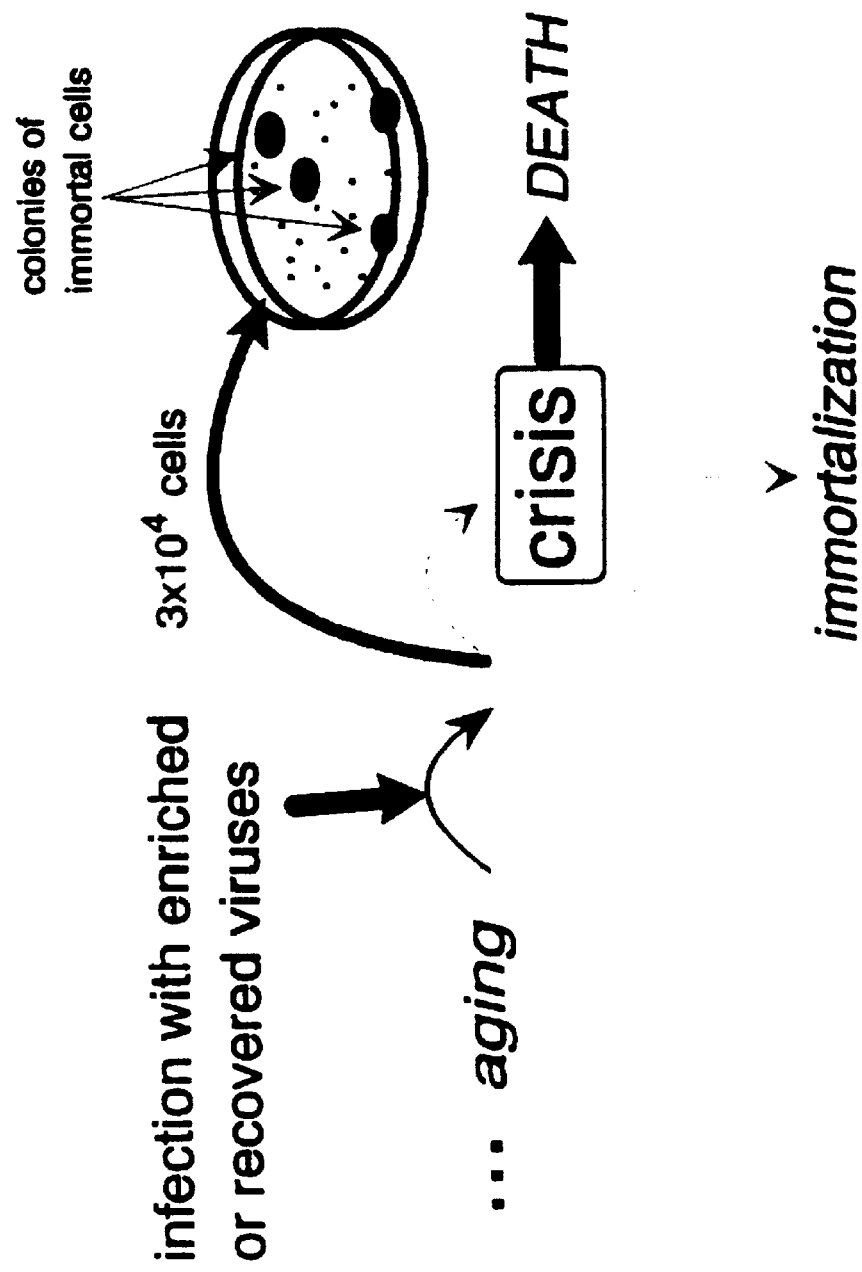

These inserts are each individually subcloned into the pLNCX retroviral vector and tested for the ability to immortalize MEF cells as shown in FIG. 3B. MEFs that are two passages before crisis are infected by GSE-carrying viruses and then plated at low density (e.g., $3 \times 10^4$ cells/100 mm culture plate) and then fixed and stained two weeks after plating. The number of surviving colonies reflects the proportion of immortalized cells in the infected population.

B. Isolation of GSEs that Can Morphologically Transform Mouse Fibroblasts

To isolate GSEs capable of inducing morphological transformation of immortalized MEFs, immortalized MEF cells as described in subsection A above were used. Cells were plated into 10 P100 plates at a density of $2.5 \times 10^6$ cells/plate and maintained in DMEM/10% FCS for three weeks. 2–20 foci of morphologically-transformed cells appeared in each plate. Two foci were isolated and expanded by growth in culture. Cells from these expanded foci were then fused with packaging cells and the hybrid cells selected with G418 and used to rescue retroviral populations as described above. Viruses isolated in this way from the expanded foci were used to infect fresh Swiss 3T3 cells, and the infected cells were maintained in DMEM/5% FCS.

Viruses rescued from each of these two foci, isolated from one of the original plates of immortalized MEF cells, induced morphological transformation of Swiss 3T3 cells in two separate experiments. PCR analysis of the cDNA insert present in the transforming virus (termed Tr6-GSE), performed on genomic DNA isolated from four independent foci of transformed Swiss 3T3 cells, revealed a single insert band. DNA from this band was re-cloned into the pLNCX vector and the nucleotide sequence determined using conventional techniques (see Sambrook et al., ibid.). This clone was found to contain a 285 bp insert (shown in FIG. 5), which showed no significant homology with known nucleic acid and protein sequences present in the National Center for Biotechnology Information database. The re-cloned Tr6-GSE-carrying retrovirus was efficient in inducing morphological transformation of NIH 3T3 cells and immortalized MEF (shown in FIG. 6A). Infection of senescent MEF cells with this virus produced no significant increase in the number of immortalized cells, relative to background.

Figure 6B:
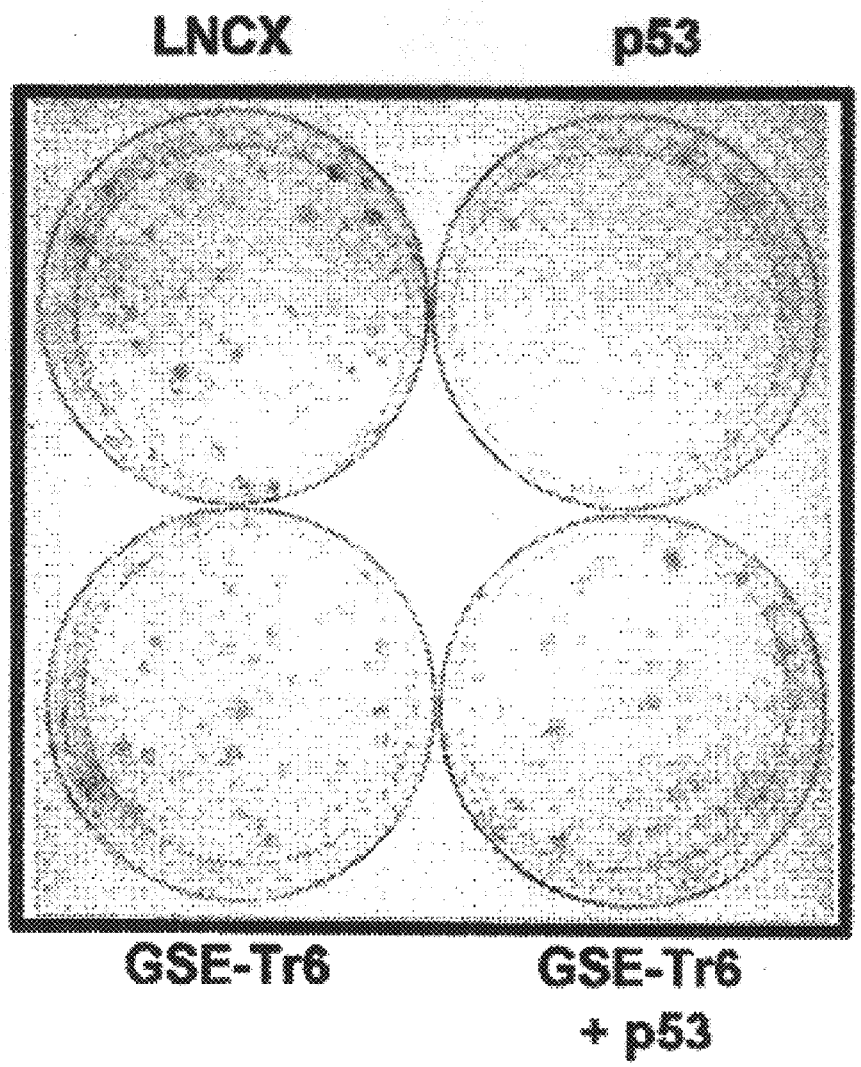

Tr6, however, was found to have an effect on MEF immortalization by a different assay. In this assay, MEF cells 2 passages from senescence were infected with LNCX, or LNCX carrying Tr6-GSE, or a retroviral construct carrying a full-length cDNA encoding the cellular tumor suppressor gene p53, or a combination of the p53 retrovirus and Tr6-GSE carrying retrovirus. MEF cells infected with the LNCX vector retrovirus produced a low background spontaneously-immortalized cells (FIG. 6B). In contrast, MEF cells infected with the recombinant retrovirus carrying a full-length cDNA of the p53 tumor suppressor gene under conditions where all the cells were infected, failed to give rise to any immortalized colonies. However, when the same cells were infected under the same conditions with retroviruses carrying Tr6 and p53, immortalized colonies were formed (FIG. 6B).

Figure 7:
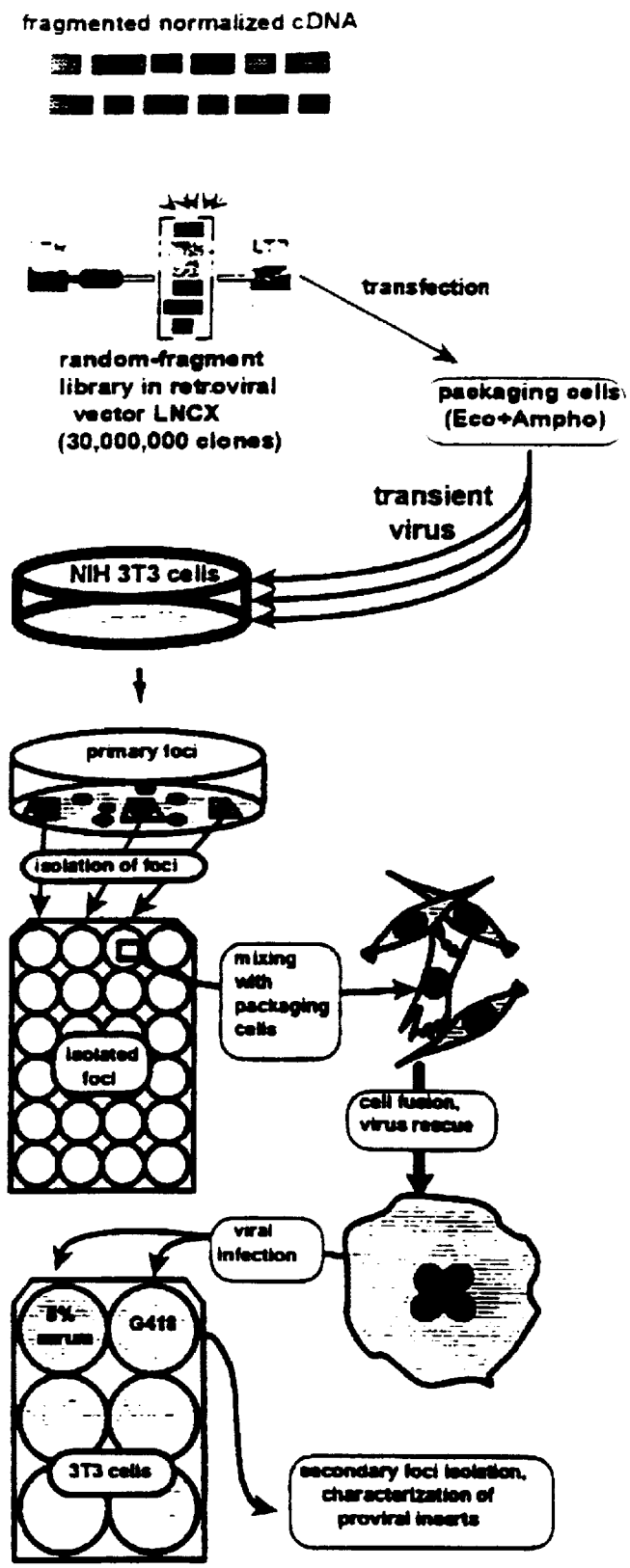
FIG. 7 shows a scheme for selecting morphological transformation-conferring GSEs.

GSEs, were also selected for the ability to induce morphological transformation of NIH 3T3 cells (shown in FIG. 7). In these experiments, RFRL plasmid DNA was transfected into a 1:1 mixture of ecotropic and amphotropic virus-packaging cells. Retroviral particle-containing tissue culture media supernatant was collected at 24, 48 and 72 h after infection and used for repeat infection of NIH 3T3 cells. The total amount of virus used for infection was estimated to be $>10^7$ infectious units. Recipient NIH 3T3 cells were plated in ten P150 plates at a density of $1 \times 10^6$ cells/plate and incubated in DMEM/10% FCS. Four plates were infected with control virus containing no GSE insert, produced by transient transfection of packaging cells with the vector plasmid pLNCX, to estimate the rate of spontaneous (i.e., non-GSE mediated) transformation in these cells.

Figure 8A:
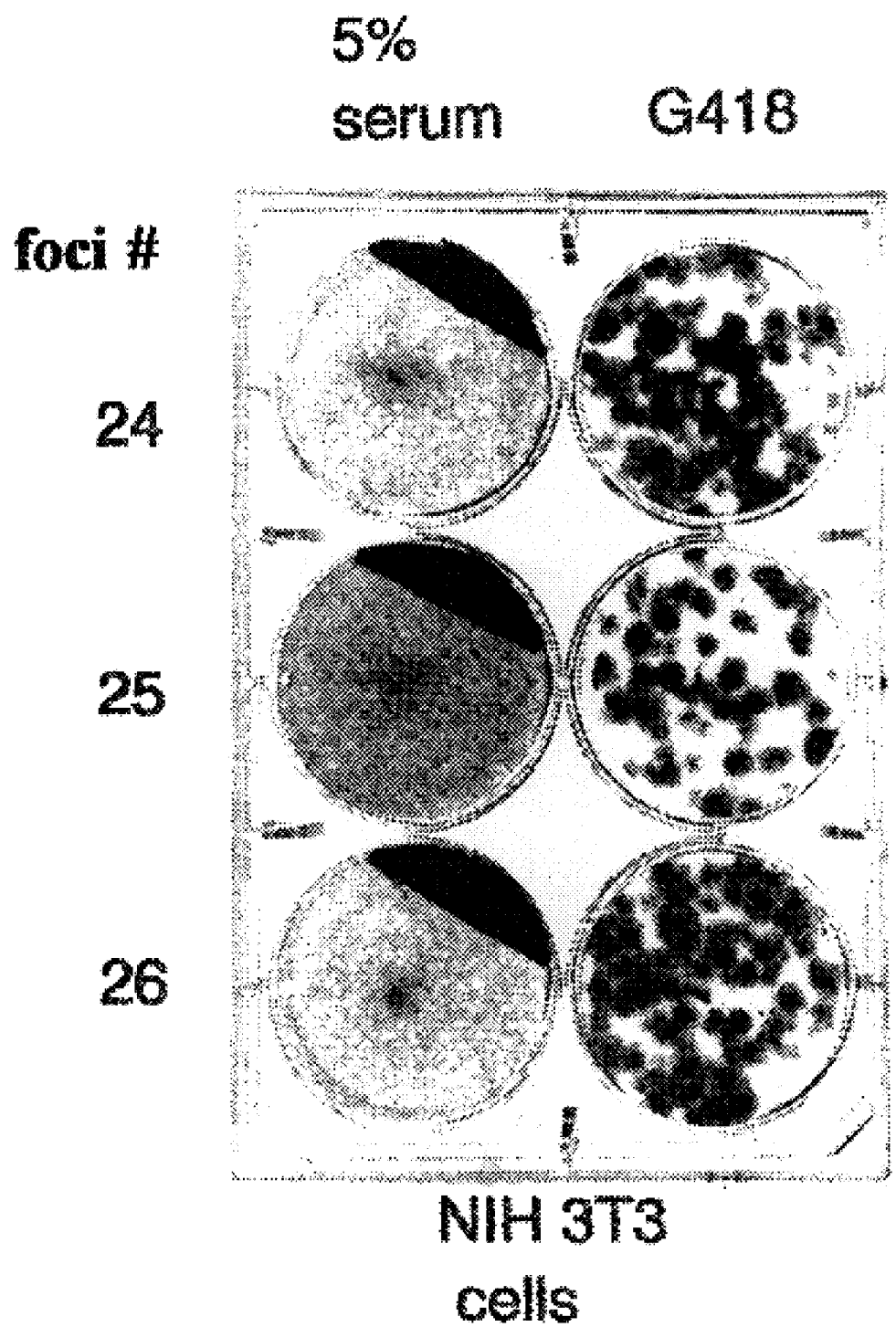
FIGS. 8A and 8B shows the results of an experiment in which rescued transforming GSE-crying retroviruses were used to re-infect fresh NIH 3T3 cells.
Figure 8B:
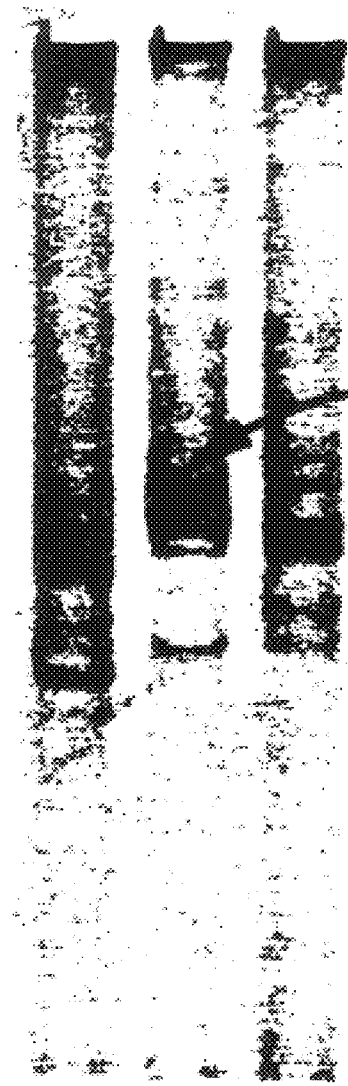

The day after the last infection, a portion of the infected NIH 3T3 cells were frozen is described above, and another portion was split into 10 P150 culture plates at a density of $2 \times 10^6$ cells/plate and cultured in DMEM/5% FCS for two weeks. The efficiency of infection was evaluated by G418 selection; typically, at least 50% of the cells were found to be infected. Similar numbers of apparently transformed cells were observed in both the experimental and control plate (5–15 foci/plate, corresponding to $2.5–7.5 \times 10^{-6}$ foci/cell). Individual foci were picked and expanded as described above, and virus rescued from each focus by fusion with ecotropic packaging cells. Fresh NIH 3T3 cells were infected with rescued retrovirus, and cells infected with 2/50 rescued virus populations were found to produce cell populations which showed altered growth properties, including reaching a much higher density in 5% serum (shown in FIG. 8). PCR analysis of genomic DNA from these populations showed that each of the two virus preparations inducing such altered cellular growth properties carried a single cDNA insert.

The two cDNA inserts carried by the transforming retroviruses isolated in this manner were sequenced and analyzed for homology with known nucleic acid and protein sequences present in the NCBI database. This analysis showed that one of the transforming viruses carried a 285 bp fragment corresponding to the beginning of the coding region of the cDNA encoding the enzyme S-adenosyl homocysteine hydrolase (SAHH), cloned in the sense orientation (shown in FIGS. 9–11). SAHH is known to be involved in many biochemical pathways, including methionine, cysteine and S-adenosylmethionine synthesis, the latter compound being the major source of methyl groups in methylation reactions. Abnormal SAHH expression may cause general alterations in cellular DNA methylation patterns and is known to alter various cellular characteristics (see Wolos et al., 1993, *J. Immunol.* 150: 3264–3273; Liu et al., 1992, *Antivir. Res.* 19: 247–265; Duerre et al., 1992, *Biochim. Biolog. Cellulaire* 70: 703–711). The SAHH-derived cDNA insert from this experiment was re-cloned into the pLNCX vector in the same orientation as in the original provirus (i.e., in the sense orientation) and used for further testing as described below.

The insert from the second transforming virus preparation was found to contain two different linked cDNA fragments, connected on one another by the adaptor. One of these fragments was derived from a cDNA encoding a structural protein, filamin. The sequence of the other fragment, termed Tr19-GSE (shown in FIG. 12) had no significant homology with any known genes in the NCBI database. These two fragments were re-cloned separately into the pLNCX retroviral vector for further testing.

Figure 13A:
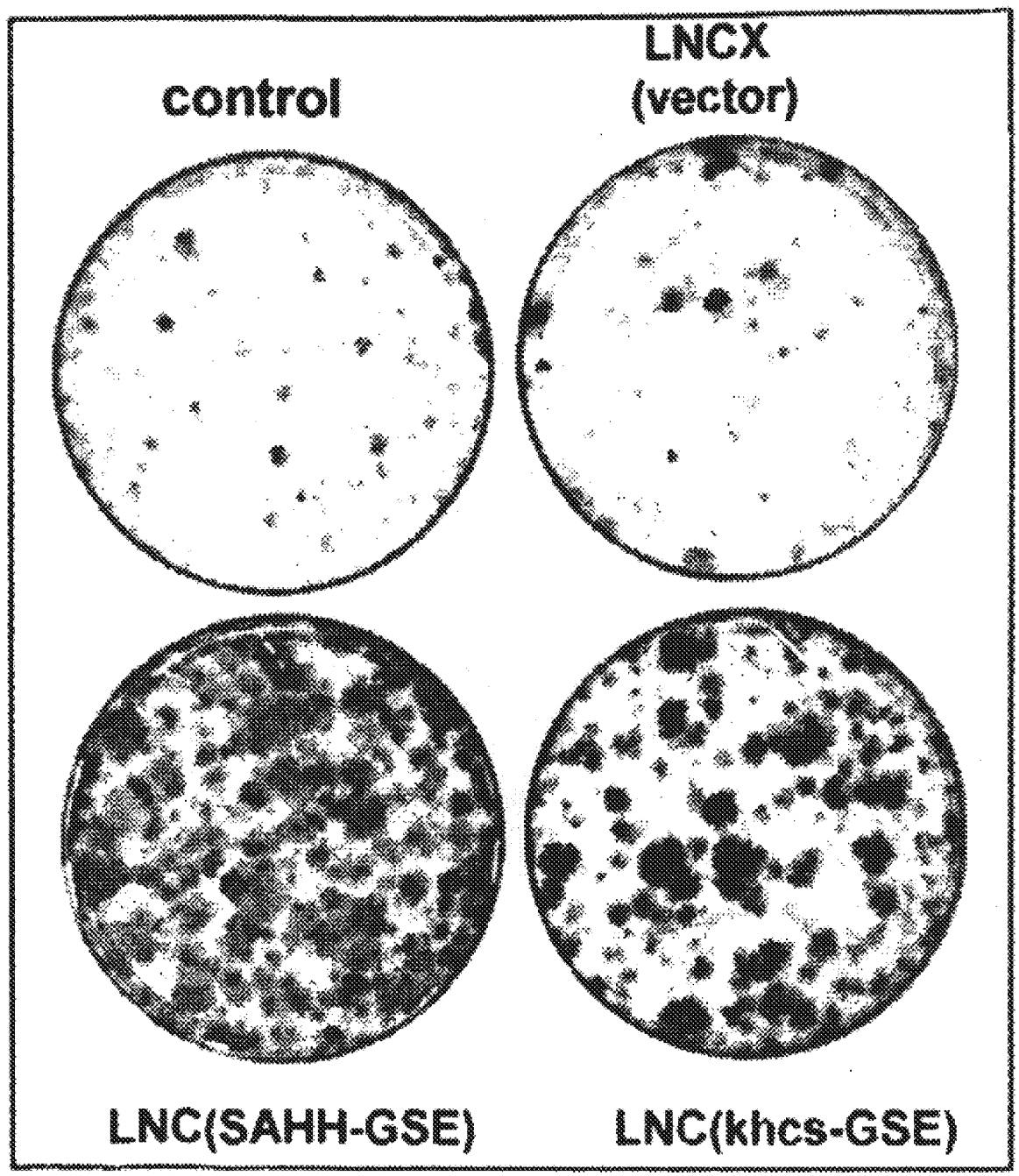
FIGS. 13A through 13C shows the results of an experiment demonstrating.
Figure 13B:
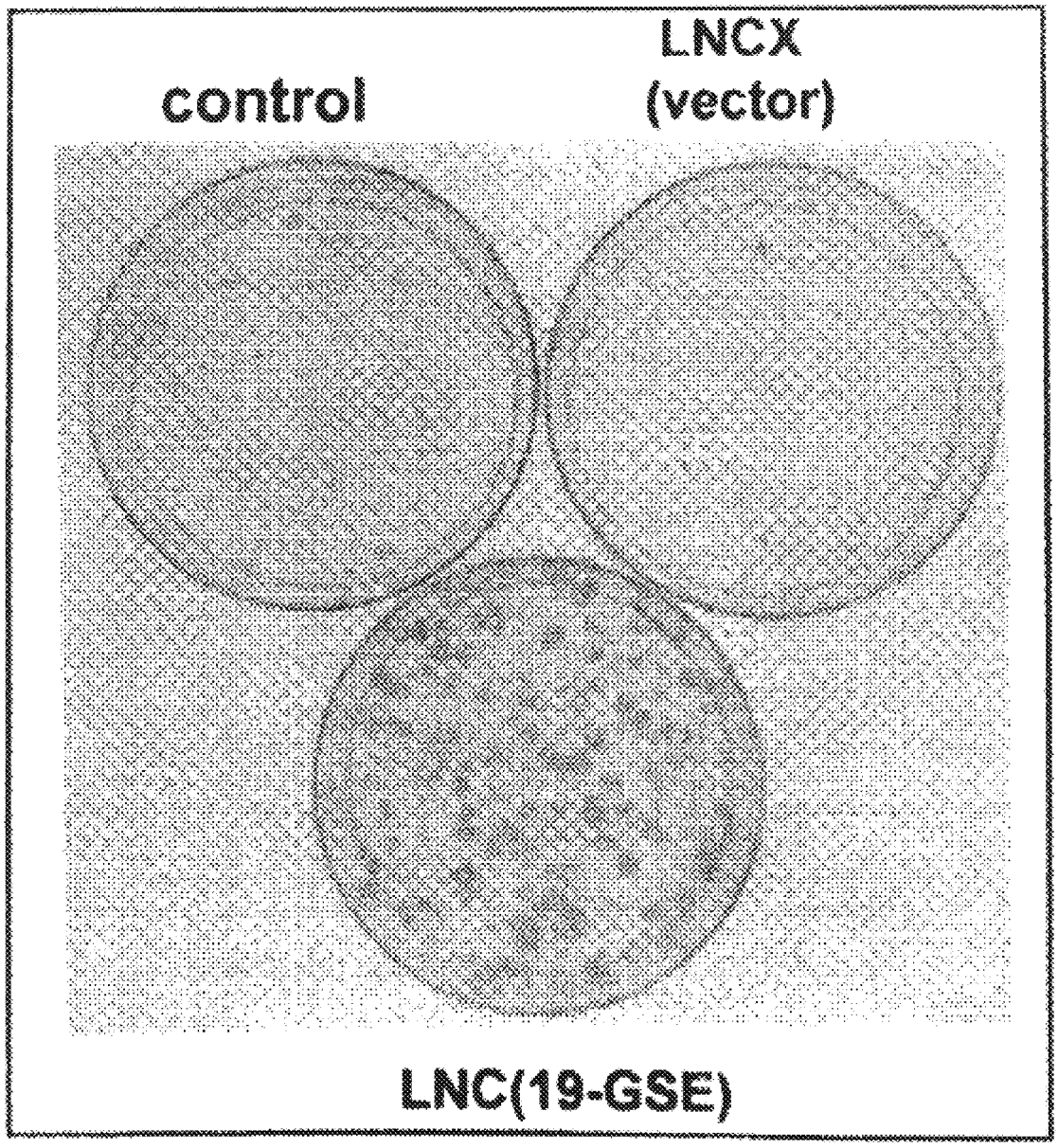
Figure 13C:
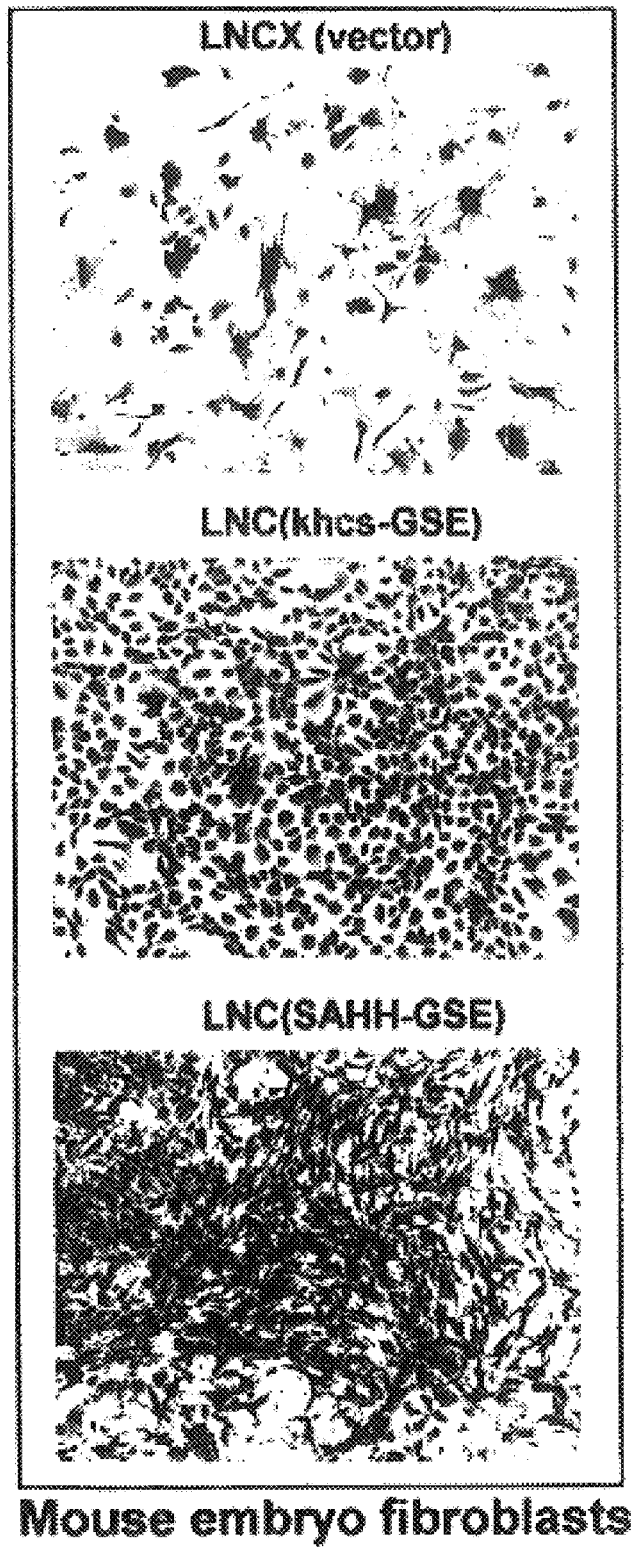

Each of the re-cloned cDNA fragments were tested by transfection into ecotropic packaging cells and the resulting virus used to infect NIH 3T3 cells (to test for morphological transformation capacity for each cDNA insert) and MEF cells (to test for both immortalization and morphological transformation capacities). The NIH 3T3 cell experiments produced highly variable results. The MEF cell experiments, on the other hand, were more efficient and reproducible, and the results of these experiments are shown in FIG. 13. Infection with virus carrying SAHH cDNA sequences (SAHH-GSE) resulted in both immortalization and morphological transformation of MEF cells. Infection with virus carrying the filamin cDNA fragment had no effect on MEF cells, but the Tr19-GSE-carrying virus was found to be capable of inducing immortalization of MEF cells, although at a lower efficiency than the SAHH-GSE. These results confirmed that the strategy disclosed herein had resulted in the isolation of two transforming, GSEs, one of which was previously unknown (Tr19) and the other derived from a gene which, although known, had not been implicated in neoplastic transformation until now.

C. Selection of GSEs Enabling Tumorigenic Growth in Nude Mice

Figure 14:
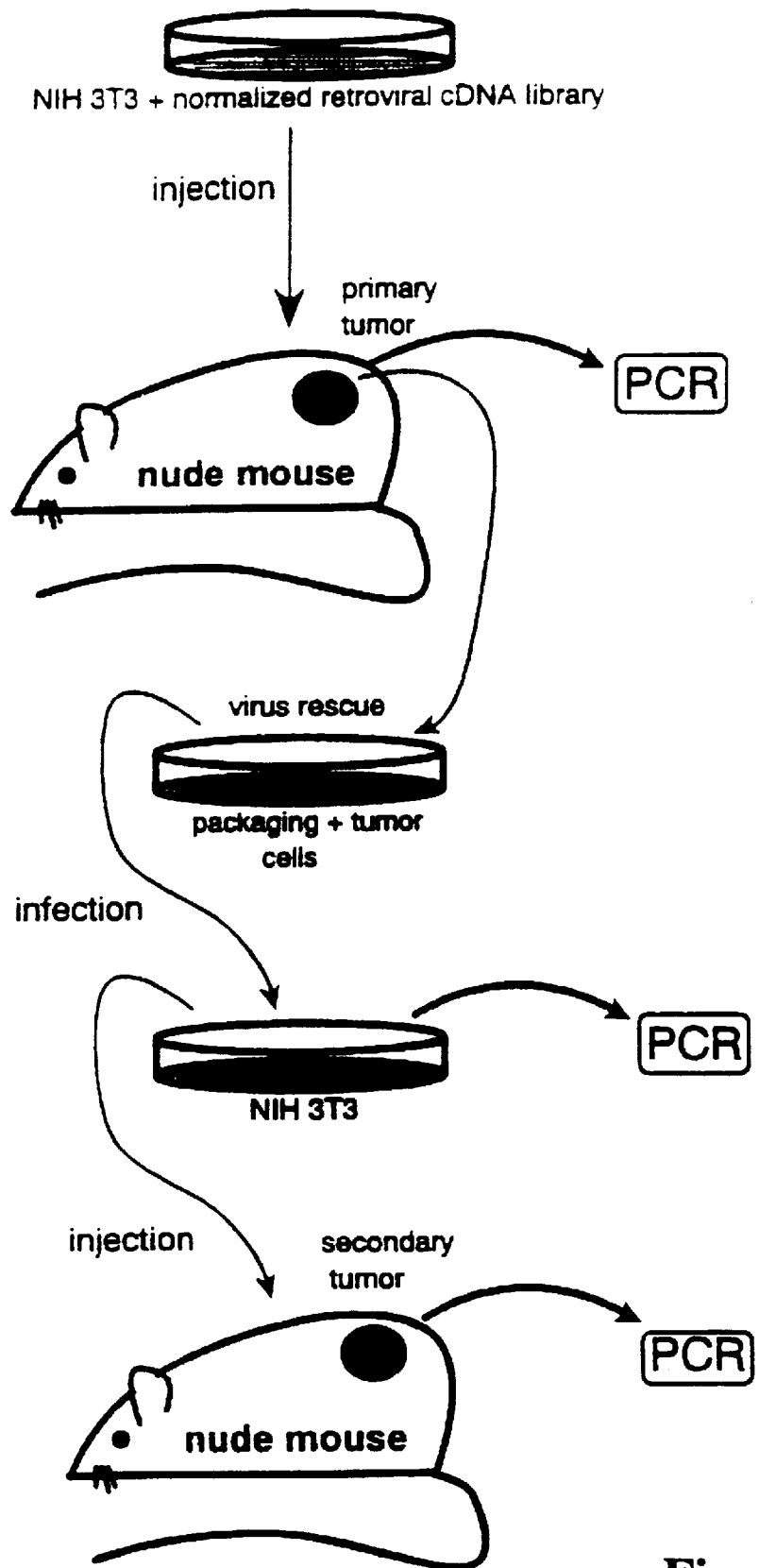
FIG. 14 shows a scheme for selecting tumorigenic GSEs.
Figure 15:
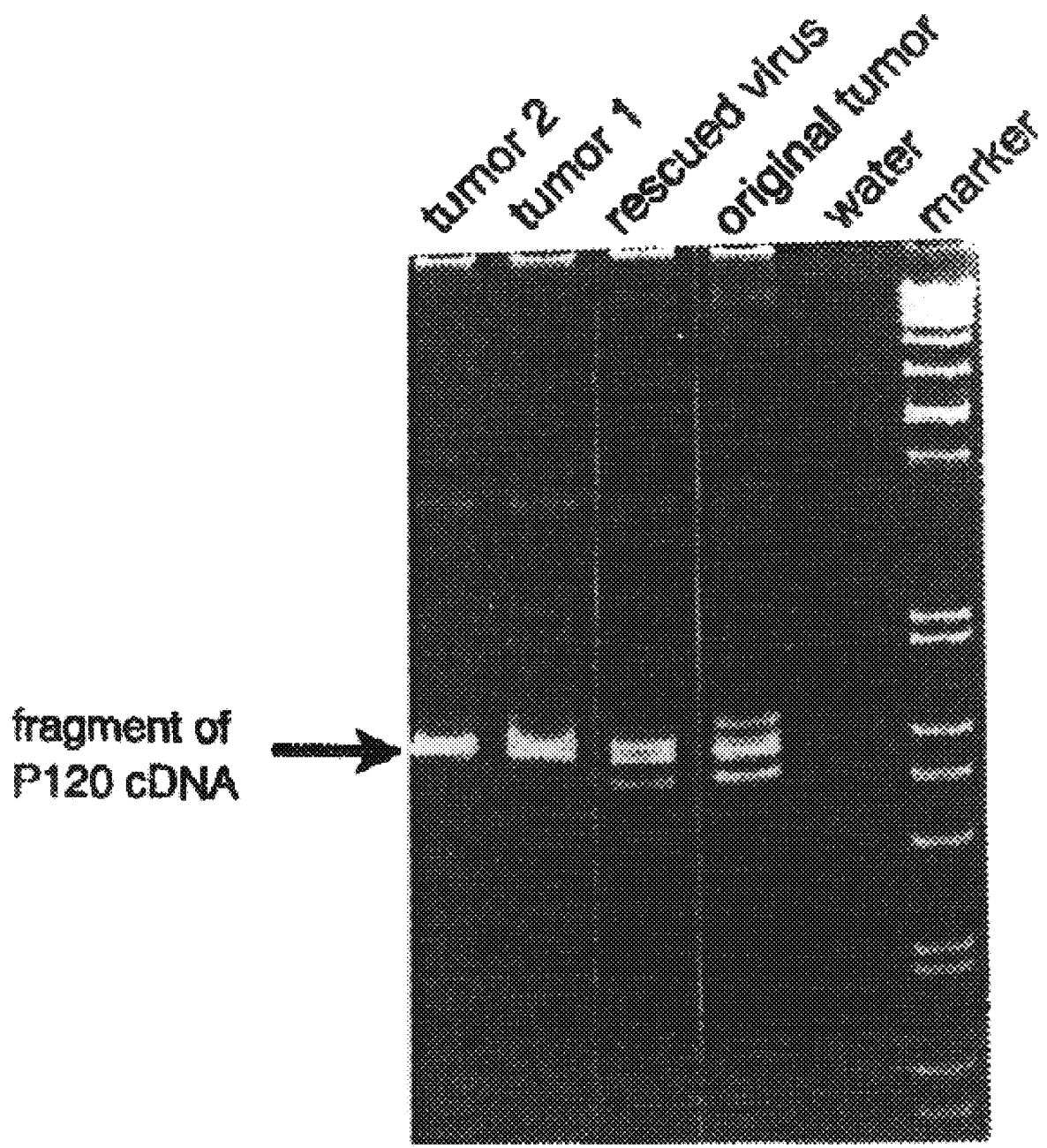
FIG. 15 polyacrylamide gel electrophoretic analysis of PCR fragments comprising tumorigenic GSEs.

The following experiments were performed to isolate GSEs capable of enabling tumorigenic growth of NIH 3T3 cells in immuno-incompetent, nude (nu/nu) mice. The scheme for these experiments is shown in FIG. 14. For this selection, RFRL-infected NIH 3T3 cells, prepared as described above, were inoculated subcutaneously into the flank of nude mice (Balb/c strain), at $5 \times 10^5$ cells per mouse. NIH 3T3 cells infected with pLNCX-vector derived virus were used as a control. Mice were examined weekly for tumor formation for up to six weeks post-inoculation. The results of these experiments are summarized in Table II.

TABLE II

| | Number of Tumor-bearing Mice | | | | |
|---|---|---|---|---|---|
| Cell Type | Week 2 | Week 3 | Week 4 | Week 5 | Week 6 |
| Control | 0/3 | 0/3 | 0/3 | 1/3 | 1/3 |
| RFRL | 0/9 | 6/9 | 7/9 | 9/9 | 9/9 |

These results, showing a higher frequency of tumorigenic variants among the NIH 3T3 cells infected with the RFRL-derived retrovirus than the LNCX-derived retrovirus, indicated the existence of tumorigenic GSEs in the population of RFRL-derived retroviruses. When the tumor size reached 5 mm in diameter, each tumor was explanted and established in culture. PCR analysis performed using genomic DNA from three of these tumor-derived cultures showed the presence of several proviruses carrying different cDNA inserts. Virus was then rescued from these tumor cells by fusion of the tumor cells with ecotropic packaging cells, as described above, infection of fresh NIH 3T3 cells and selection in nude mice for tumorigenicity. Two mice were used per each transduced cell population, and proviral inserts from tumors formed in these mice were characterized by PCR analysis (shown in FIG. 15). In two of the three populations tested, a single insert was found to be enriched in the secondary tumors of both independently-injected mice. A different insert was detected in the secondary tumors of mice injected with cells infected with virus derived from the third original NIH 3T3 cell population.

Both of these putative tumorigenic GSEs were characterized by nucleotide sequencing and the sequences compared with known nucleic acid and protein sequences present in the NCBI database. One of the cDNA inserts, termed Tr22-GSE, was found to share no significant homology with any of the sequences in the database, and hence represents a fragment of a novel gene (this sequence is shown in FIG. 16). The other cDNA insert, termed 1bb1-GSE, is a sense-oriented GSE that encodes 87 amino acids from the internal region of the mouse homolog of the human P120 nucleolar antigen of proliferating cells. The nucleotide sequence of this GSE is shown in FIG. 17, and nucleic acid and amino acid sequence comparisons between the P120 sequence and the GSE sequence are shown in FIGS. 18 and 19, respectively.

The 1bb1 fragment was re-cloned into the pLNCX vector, transfected into ecotropic packaging cells, and the resulting virus used to infect Swiss 3T3 cells. Infection with the 1bb1-carrying virus resulted in the formation of morphologically-transformed foci in these cells (FIG. 20). These results are consistent with a recent report that a full-length cDNA of P120 is capable of acting as a dominant oncogene in NIH 3T3 cells (Perlaky et al., 1992, *Cancer Res.* 52: 428–436). The results disclosed herein indicate that the portion of the P120 cDNA comprising the 1bb1 GSE encodes a functional oncogenic domain representing about 10% of the P120 protein. This result is the first demonstration that such a small portion of an oncogenic protein is oncogenically functional.

EXAMPLE 3

Cloning and Analysis of the Genes from which Each Transforming GSE was Derived

The results described in Example 2 above discloses the isolation of three newly-identified genes implicated in cellular transformation in tumor cells. Each of the genes corresponding to these three GSEs are isolated as follows. Each GSE is used as a hybridization probe to screen a mouse or human cDNA library prepared from normal cells. Interspecific DNA hybriudization at the appropriate stringency is expected to enable the isolation of genes corresponding to GSEs from any mammalian species, using nucleic acid probes that are homologous to GSEs or genes corresponding to such GSEs isolated as described in Example 2 above. The nucleotide sequence of the longest cDNA clone isolated in this way for each GSE is then determined, and the sequence analyzed to identify the longest open reading frame (ORF) encoding the putative gene product from each strand. Sequence homology analysis, as described above, is then performed on the sequence of the longest ORF to determine whether a related protein has been previously identified. If necessary, any additional nucleotides encoding amino acids from the amino terminus are then determined from 5'-specific cDNA isolated using the "anchored PCR" technique, as described by Ohara et al. (1989, *Proc. Natl. Acad. Sci. USA* 86: 5763–5677). Additional missing 3' terminal sequences are also isolated using this technique. The "anchored PCR" technique can also be used to isolate full-length cDNA starting directly from the GSE sequence without library screening.

It should be understood that the foregoing disclosure emphasizes certain specific embodiments of the invention and that all modifications or alternatives equivalent thereto are within the spirit and scope of the invention as set forth in the appended claims.

What is claimed is:

1. A sense-oriented genetic suppressor element encoding a peptide that establishes or maintains a transformed phenotype in a mammalian cell wherein the genetic suppressor element is identified by a method of isolating genetic suppressor elements, wherein the method comprises the steps of:

(a) synthesizing randomly fragmented cDNA prepared from the total mRNA of a cell to yield DNA fragments;

(b) transferring the DNA fragments to an expression vector to yield a genetic suppressor element library, wherein the expression vector expresses the DNA fragments in a living cell;

(c) genetically modifying the living cells by introducing the genetic suppressor element library into the cells;

(d) isolating or enriching for genetically modified living cells containing genetic suppressor elements conferring the transformed phenotype on the cells by selecting the cells under conditions wherein the transformed cells are identifiable;

(e) obtaining the genetic suppressor element conferring the transformed phenotype from the surviving genetically modified cells.

2. A mammalian cell that expresses the genetic suppressor element according to claim 1.

3. A sense-oriented genetic suppressor element comprising a nucleotide sequence selected from the group consisting of Sequence I.D. Nos. 3, 4, 8, 9, and 10.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

AATCATCGAT GGATGGATGG                                                      20

(2) INFORMATION FOR SEQ ID NO:2:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

CCATCCATCC ATCGATGATT AAA                                                  23

(2) INFORMATION FOR SEQ ID NO:3:

(i) SEQUENCE CHARACTERISTICS:
       (A) LENGTH: 285 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:3:

GTTATGTAAC CCTGGCTATT CTGGAACTTG ATATCTAGAC CAGGCTGGCC TTGAACTCAA            60

ACAGATATCT TCCTGTTTCT GTCTCCTTAG TGCTGGGATA CAGTGTTTAG TGCTGCCATG           120

CTGGGTGGGA AGAGTATAAT AATAGCTCAT AGTTACTATG TTTGTTTAGG TTAGACATTT           180

TTTTTTCTGC TTTGTGTGTC TAATATGTTT GAACATCTCA TCTTCTTGAA ACTTGATGTG           240

GCTGTGTGAT TTGCTTTGGT TATTGAAAAG TGGCACATTG GCCAT                           285

(2) INFORMATION FOR SEQ ID NO:4:

(i) SEQUENCE CHARACTERISTICS:
       (A) LENGTH: 210 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:4:

AACACGCCGT ACTTCCTCTG CTCAGCCCGT CTTTCCTCAT CATTGACCTT TTGTGTAGGC            60

AAGAGAACCC TCTGGGTGCA GTTTCATCTG CGGCTAAAGG ATCTCGCTGG CTCCGGTGGA           120

CCAGGTGAAA AGACACAGCT TTCTTCTTCT CTATAAAGGG CTTTTTCTTT CTGTGAGGCA           180

TAATGAGGCA GGGACACCCT CTCCGGAACC                                              210

(2) INFORMATION FOR SEQ ID NO:5:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGATGATGGA GGTGGCAGCT GCCGATGTCC AGAGGCTGGG GGGCTCCGTG GAACTGGTGG    60

ATATCGGGAA GCAGAAGCTC CCAGATGGCT CGGAGATACC ACTTCTCCCA TCTGCTGGGC    120

AAGCTAGGCA GCGACCCCCA GAAGAAAACC GTGTGCATTT ACGGGCACCT GGACGTGCAG    180

CCTGCGCCCT GGAGGACGGG TGGGACAGCG AGCCCTTCAC CTTGGTGGAG CGGGAAGGCA    240

AGCTGTATGG GAGAGGCTCC ACGGACGATA AGG                                 273

(2) INFORMATION FOR SEQ ID NO:6:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CATTCACTGA GTTCATCAGT CCTAGCGGAA GCCGCCAGCA TGTCTGATAA ACTGCCCTAC    60

AAAGTCGCGG ACATCGGACT GGCCGCCTGG GGACGGAAGG CTCTGGATAT AGCTGAGAAT    120

GAGATGCCAG GGTTGATGCG CATGCGGGAG ATGTACTCAG CCTCCAAGCC ACTGAAGGGT    180

GCTCGCATTG CTGGCTGCCT GCGCATGACC GTGGAGACTG CTGTTCTCAT TGAGACTCTC    240

GTGGCCCTGG GTGCTGAGGC GCGGTGGTCC AGCTGCAACA TCTTC                    285

(2) INFORMATION FOR SEQ ID NO:7:

(i) SEQUENCE CHARACTERISTICS:
        (A) LENGTH: 97 amino acids
        (B) TYPE: amino acid
        (D) TOPOLOGY: linear (ii) MOLECULE TYPE: peptide (xi) SEQUENCE DESCRIPTION: SEQ ID NO:7:

Glu Ala Gln Pro Pro Ser Pro Val Ser Ile Thr Ser Ala Ala Ser Met
    1               5                   10                  15

Ser Asp Lys Leu Pro Tyr Lys Val Ala Asp Ile Gly Leu Ala Ala Trp
                    20                  25                  30

Gly Arg Lys Ala Leu Asp Ile Ala Glu Asn Glu Met Pro Gly Leu Met
                35                  40                  45

Arg Met Arg Glu Arg Tyr Ser Ala Ser Lys Pro Leu Lys Gly Ala Arg
        50                  55                  60

Ile Ala Gly Cys Leu His Met Thr Val Glu Thr Ala Val Leu Ile Glu
    65                  70                  75                  80

Thr Leu Val Thr Leu Gly Ala Glu Val Gln Trp Ser Ser Cys Asn Ile
                    85                  90                  95

Phe (2) INFORMATION FOR SEQ ID NO:8:

(i) SEQUENCE CHARACTERISTICS:
       (A) LENGTH: 289 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:8:

```
GGCCCAGCCC CCTTCGCCCG TTTCCATCAC GAGTGCCGCC AGCATGTCTG ACAAACTGCC        60

CTACAAAGTC GCCGACATCG GCCTGGCTGC CTGGGGACGC AAGGCCCTGG ACATTGCTGA       120

GAACGAGATG CCGGGCCTGA TGCGTATGCG GGAGCGGTAC TCGGCCTCCA AGCCACTGAA       180

GGGCGCCCGC ATCGCTGGCT GCCTGCACAT GACCGTGGAG ACGGCCGTCC TCATTGAGAC       240

CCTCGTCACC CTGGGTGCTG AGGTGCAGTG GTCCAGCTGC AACATCTTC                   289
```

(2) INFORMATION FOR SEQ ID NO:9:

(i) SEQUENCE CHARACTERISTICS:
       (A) LENGTH: 95 amino acids
       (B) TYPE: amino acid
       (D) TOPOLOGY: linear (ii) MOLECULE TYPE: protein (xi) SEQUENCE DESCRIPTION: SEQ ID NO:9:

```
His Ser Leu Ser Ser Val Leu Ala Glu Ala Ala Ser Met Ser Asp
 1               5                  10                  15

Lys Leu Pro Tyr Lys Val Ala Asp Ile Gly Leu Ala Ala Trp Gly Arg
                20                  25                  30

Lys Ala Leu Asp Ile Ala Glu Asn Glu Met Pro Gly Leu Met Arg Met
                35                  40                  45

Arg Glu Met Tyr Ser Ala Ser Lys Pro Leu Lys Gly Ala Arg Ile Ala
                50                  55                  60

Gly Cys Leu Arg Met Thr Val Glu Thr Ala Val Leu Ile Glu Thr Lys
 65                  70                  75                  80

Val Ala Leu Gly Ala Glu Ala Arg Trp Ser Ser Cys Asn Ile Phe
                85                  90                  95
```

(2) INFORMATION FOR SEQ ID NO:10:

(i) SEQUENCE CHARACTERISTICS:
       (A) LENGTH: 263 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:10:

```
CCCGGCCAAT CACCCTTCGG ACCAACACCT TGAAACCCG TCGCCGAGAC CTTGCTCAGG         60

CTCTGATCAA TCGTGGGGTT AATCTGGATC CACTGGGGAA GTGGTCAAAG TCTGGACTTG       120

TGGTATATGA TTCTTCAGTG CCTATTGGTG CTACCCCTGA GTACCTCGCT GGACACTATA       180

TGCTGCAGGG AGCTTCCAGT ATGTTGCCCG TCATGGCCCT GGCACCTCAG GAGCATGAGC       240

GGATCTTAGA CATGTGCTGT GCT                                               263
```

(2) INFORMATION FOR SEQ ID NO:11:

(i) SEQUENCE CHARACTERISTICS:
    (A) LENGTH: 108 amino acids
    (B) TYPE: amino acid
    (D) TOPOLOGY: linear (ii) MOLECULE TYPE: peptide (xi) SEQUENCE DESCRIPTION: SEQ ID NO:11:

```
Lys Leu Met Asp Leu Phe Pro Leu Ser Glu Leu Val Glu Phe Leu Glu
 1               5                  10                  15

Ala Asn Glu Val Pro Arg Pro Val Thr Leu Arg Thr Asn Thr Leu Lys
            20                  25                  30

Thr Arg Arg Arg Asp Leu Ala Gln Ala Leu Glu Asn Arg Gly Val Asn
        35                  40                  45

Leu Asp Pro Leu Gly Lys Trp Ser Lys Thr Gly Leu Val Val Tyr Asp
    50                  55                  60

Ser Ser Val Pro Ile Gly Ala Thr Pro Glu Tyr Leu Ala Gly His Tyr
65                  70                  75                  80

Met Leu Gln Gly Ala Ser Ser Met Leu Pro Val Met Ala Leu Ala Pro
                85                  90                  95

Gln Glu His Glu Arg Ile Leu Asp Met Cys Cys Ala
            100                 105
```

(2) INFORMATION FOR SEQ ID NO:12:

(i) SEQUENCE CHARACTERISTICS:
    (A) LENGTH: 262 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:12:

```
CTCGGCCCGT CACCCTCCGG ACCAATACCT TGAAAACCCG ACGCCGAGAC CTTGCACAGG    60

CTCTAATCAA TCGTGGGGTT AACCTGGATC CCCTGGGCAA GTGGTCAAAG ACTGGACTAG   120

TGGTGTATGA TTCTTCTGTG CCCATTGGTG CTACCCCCGA GTACCTGGCT GGGCACTACA   180

TGCTGCAGGG AGCCTCCAGC ATGTTGCCCG TCATGGCCTT GGCACCCCAG GAACATGAGC   240

GGATCCTGGA CATGTGTTGT GC                                            262
```

(2) INFORMATION FOR SEQ ID NO:13:

(i) SEQUENCE CHARACTERISTICS:
    (A) LENGTH: 87 amino acids
    (B) TYPE: amino acid
    (D) TOPOLOGY: linear (ii) MOLECULE TYPE: peptide (xi) SEQUENCE DESCRIPTION: SEQ ID NO:13:

```
Arg Pro Val Thr Leu Arg Thr Asn Thr Leu Lys Thr Arg Arg Arg Asp
 1               5                  10                  15

Leu Ala Gln Ala Leu Ile Asn Arg Gly Val Asn Leu Asp Pro Leu Gly
            20                  25                  30

Lys Trp Ser Lys Thr Gly Leu Val Val Tyr Asp Ser Ser Val Pro Ile
        35                  40                  45

Gly Ala Thr Pro Glu Tyr Leu Ala Gly His Tyr Met Leu Gln Gly Ala
    50                  55                  60

Ser Ser Met Leu Pro Val Met Ala Leu Ala Pro Gln Glu His Glu Arg
```

```
                65                 70                75                80
         Ile Leu Asp Met Cys Cys Ala
                            85

(2) INFORMATION FOR SEQ ID NO:14:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

ATGGATGGAT GG                                                          12

(2) INFORMATION FOR SEQ ID NO:15:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

CCATCCATCC AT                                                          12
```